(12) United States Patent
Stone et al.

(10) Patent No.: US 8,292,921 B2
(45) Date of Patent: Oct. 23, 2012

(54) SOFT TISSUE REPAIR DEVICE AND ASSOCIATED METHODS

(75) Inventors: Kevin T. Stone, Winona Lake, IN (US);
Ryan A. Kaiser, Leesburg, IN (US);
Nathan M. Sautter, North Manchester, IN (US); Andrew Holst, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/045,691

(22) Filed: Mar. 11, 2011

(65) Prior Publication Data
US 2011/0160768 A1 Jun. 30, 2011

Related U.S. Application Data

(60) Division of application No. 12/014,399, filed on Jan. 15, 2008, now Pat. No. 7,909,851, which is a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/347,661, filed on Feb. 3, 2006, now Pat. No. 7,749,250, which is a continuation-in-part of application No. 11/408,282, filed on Apr. 20, 2006, now abandoned, and a continuation-in-part of application No. 11/541,506, filed on Sep. 29, 2006, now Pat. No. 7,601,165.

(60) Provisional application No. 60/885,062, filed on Jan. 16, 2007, provisional application No. 60/885,057, filed on Jan. 16, 2007.

(51) Int. Cl.
*A61B 17/04* (2006.01)
(52) U.S. Cl. ...................................................... 606/232
(58) Field of Classification Search .................. 606/300, 606/213–216, 233, 232, 139; 623/13.11, 623/14.12
See application file for complete search history.

(56) References Cited

U.S. PATENT DOCUMENTS

| | | | |
|---|---|---|---|
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 401,677 | A | 4/1889 | Autenreith |

(Continued)

FOREIGN PATENT DOCUMENTS

AU 4957264 3/1966

(Continued)

OTHER PUBLICATIONS

"AperFix® System Surgical Technique Guide. Single Tunnel Double Bundle.™" Cayenne Medical brochure. (Aug. 2008) 8 sheets.

(Continued)

*Primary Examiner* — Dianne Dornbusch
(74) *Attorney, Agent, or Firm* — Harness, Dickey

(57) ABSTRACT

A method for repairing a defect in a fibrous soft tissue includes passing a distal portion of an inserter through corresponding longitudinal bores of first and second anchors. The method includes coupling the first and second anchors with a flexible strand, and forming an adjustable knotless loop with the flexible strand.

21 Claims, 20 Drawing Sheets

U.S. PATENT DOCUMENTS

| | | |
|---|---|---|
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |

| | | |
|---|---|---|
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,074,874 A | 12/1991 | Yoon et al. |

| Patent No. | Date | Inventor |
|---|---|---|
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A * | 4/1995 | Pierce .......................... 606/232 |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A * | 11/1995 | Bonutti .......................... 606/232 |
| 5,464,427 A | 11/1995 | Curtis et al. |
| 5,464,440 A | 11/1995 | Johansson et al. |
| 5,466,237 A | 11/1995 | Byrd, III et al. |

| | | | | | | |
|---|---|---|---|---|---|---|
| 5,467,786 A | 11/1995 | Allen et al. | | 5,628,766 A | 5/1997 | Johnson |
| 5,470,334 A | 11/1995 | Ross et al. | | 5,630,824 A | 5/1997 | Hart |
| 5,470,337 A | 11/1995 | Moss | | 5,632,748 A | 5/1997 | Beck, Jr. et al. |
| 5,470,338 A | 11/1995 | Whitfield et al. | | 5,641,256 A | 6/1997 | Gundy |
| 5,472,452 A | 12/1995 | Trott | | 5,643,266 A | 7/1997 | Li |
| 5,474,565 A | 12/1995 | Trott | | 5,643,269 A | 7/1997 | Harle et al. |
| 5,474,568 A | 12/1995 | Scott | | 5,643,295 A | 7/1997 | Yoon |
| 5,474,572 A | 12/1995 | Hayhurst | | 5,643,319 A | 7/1997 | Green et al. |
| 5,478,344 A | 12/1995 | Stone et al. | | 5,643,320 A | 7/1997 | Lower et al. |
| 5,478,345 A | 12/1995 | Stone et al. | | 5,643,321 A | 7/1997 | McDevitt |
| 5,480,403 A | 1/1996 | Lee et al. | | 5,645,546 A | 7/1997 | Fard |
| 5,480,406 A | 1/1996 | Nolan et al. | | 5,645,547 A | 7/1997 | Coleman |
| 5,484,442 A | 1/1996 | Melker et al. | | 5,645,568 A | 7/1997 | Chervitz et al. |
| 5,486,197 A | 1/1996 | Le et al. | | 5,645,588 A | 7/1997 | Graf et al. |
| 5,490,750 A | 2/1996 | Gundy | | 5,647,874 A | 7/1997 | Hayhurst |
| 5,496,331 A | 3/1996 | Xu et al. | | 5,649,959 A | 7/1997 | Hannam et al. |
| 5,496,348 A | 3/1996 | Bonutti | | 5,649,963 A | 7/1997 | McDevitt |
| 5,500,000 A | 3/1996 | Feagin et al. | | 5,658,289 A | 8/1997 | Boucher et al. |
| 5,505,736 A | 4/1996 | Reimels et al. | | 5,658,299 A | 8/1997 | Hart |
| 5,507,754 A | 4/1996 | Green et al. | | 5,658,313 A | 8/1997 | Thal |
| 5,520,691 A | 5/1996 | Branch | | 5,662,658 A | 9/1997 | Wenstrom, Jr. |
| 5,520,700 A | 5/1996 | Beyar et al. | | 5,662,663 A | 9/1997 | Shallman |
| 5,520,702 A | 5/1996 | Sauer et al. | | 5,665,112 A | 9/1997 | Thal |
| 5,522,817 A | 6/1996 | Sander et al. | | 5,667,513 A | 9/1997 | Torrie et al. |
| 5,522,820 A | 6/1996 | Caspari et al. | | 5,671,695 A | 9/1997 | Schroeder |
| 5,522,844 A | 6/1996 | Johnson | | 5,674,224 A | 10/1997 | Howell et al. |
| 5,522,845 A | 6/1996 | Wenstrom, Jr. | | 5,679,723 A | 10/1997 | Cooper et al. |
| 5,522,846 A | 6/1996 | Bonutti | | 5,681,334 A | 10/1997 | Evans et al. |
| 5,524,946 A | 6/1996 | Thompson | | 5,681,352 A | 10/1997 | Clancy, III et al. |
| 5,527,321 A | 6/1996 | Hinchliffe | | 5,683,419 A | 11/1997 | Thal |
| 5,527,342 A | 6/1996 | Pietrzak et al. | | 5,688,285 A | 11/1997 | Yamada et al. |
| 5,527,343 A | 6/1996 | Bonutti | | 5,690,676 A | 11/1997 | DiPoto et al. |
| 5,534,012 A | 7/1996 | Bonutti | | 5,690,678 A | 11/1997 | Johnson |
| 5,536,270 A | 7/1996 | Songer et al. | | 5,693,046 A | 12/1997 | Songer et al. |
| 5,540,698 A | 7/1996 | Preissman | | 5,695,497 A | 12/1997 | Stahelin et al. |
| 5,540,703 A | 7/1996 | Barker, Jr. et al. | | 5,697,929 A | 12/1997 | Mellinger |
| 5,540,718 A * | 7/1996 | Bartlett .................. 606/232 | | 5,699,657 A | 12/1997 | Paulson |
| 5,545,168 A | 8/1996 | Burke | | 5,702,397 A | 12/1997 | Goble et al. |
| 5,545,178 A | 8/1996 | Kensey et al. | | 5,702,422 A | 12/1997 | Stone |
| 5,545,180 A | 8/1996 | Le et al. | | 5,702,462 A | 12/1997 | Oberlander |
| 5,545,228 A | 8/1996 | Kambin | | 5,707,373 A | 1/1998 | Sevrain et al. |
| 5,549,613 A | 8/1996 | Goble et al. | | 5,711,969 A | 1/1998 | Patel et al. |
| 5,549,617 A | 8/1996 | Green et al. | | 5,713,005 A | 1/1998 | Proebsting |
| 5,549,619 A | 8/1996 | Peters et al. | | 5,713,904 A | 2/1998 | Errico et al. |
| 5,549,630 A | 8/1996 | Bonutti | | 5,713,905 A | 2/1998 | Goble et al. |
| 5,549,631 A | 8/1996 | Bonutti | | 5,713,921 A | 2/1998 | Bonutti |
| 5,562,683 A | 10/1996 | Chan | | 5,716,359 A | 2/1998 | Ojima et al. |
| 5,562,685 A | 10/1996 | Mollenauer et al. | | 5,716,397 A | 2/1998 | Myers |
| 5,562,686 A | 10/1996 | Sauer et al. | | 5,718,717 A | 2/1998 | Bonutti |
| 5,569,269 A | 10/1996 | Hart et al. | | 5,720,747 A | 2/1998 | Burke |
| 5,569,305 A | 10/1996 | Bonutti | | 5,720,765 A | 2/1998 | Thal |
| 5,571,090 A | 11/1996 | Sherts | | 5,720,766 A | 2/1998 | Zang et al. |
| 5,571,139 A | 11/1996 | Jenkins, Jr. | | 5,722,976 A | 3/1998 | Brown |
| 5,572,655 A | 11/1996 | Tuljapurkar et al. | | 5,725,549 A | 3/1998 | Lam |
| 5,573,286 A | 11/1996 | Rogozinski | | 5,725,556 A | 3/1998 | Moser et al. |
| 5,573,542 A | 11/1996 | Stevens | | 5,725,581 A | 3/1998 | Brånemark |
| 5,573,548 A | 11/1996 | Nazre et al. | | 5,725,582 A | 3/1998 | Bevan et al. |
| 5,577,299 A | 11/1996 | Thompson et al. | | 5,726,722 A | 3/1998 | Uehara et al. |
| 5,578,057 A | 11/1996 | Wenstrom, Jr. | | 5,728,107 A | 3/1998 | Zlock et al. |
| 5,584,695 A | 12/1996 | Lal Sachdeva et al. | | 5,728,109 A | 3/1998 | Schulze et al. |
| 5,584,835 A | 12/1996 | Greenfield | | 5,728,136 A | 3/1998 | Thal |
| 5,584,836 A | 12/1996 | Ballintyn et al. | | 5,733,293 A | 3/1998 | Scirica et al. |
| 5,584,862 A | 12/1996 | Bonutti | | 5,733,306 A | 3/1998 | Bonutti |
| 5,586,986 A | 12/1996 | Hinchliffe | | 5,733,307 A | 3/1998 | Dinsdale |
| 5,588,575 A | 12/1996 | Davignon | | 5,735,875 A | 4/1998 | Bonutti et al. |
| 5,591,180 A | 1/1997 | Hinchliffe | | 5,741,259 A | 4/1998 | Chan |
| 5,591,181 A | 1/1997 | Stone et al. | | 5,741,260 A | 4/1998 | Songer et al. |
| 5,591,207 A | 1/1997 | Coleman | | 5,741,281 A | 4/1998 | Martin |
| 5,593,407 A | 1/1997 | Reis et al. | | 5,743,912 A | 4/1998 | Lahille et al. |
| 5,593,425 A | 1/1997 | Bonutti et al. | | 5,746,751 A | 5/1998 | Sherts |
| 5,601,557 A | 2/1997 | Hayhurst | | 5,746,752 A | 5/1998 | Burkhart |
| 5,601,559 A | 2/1997 | Melker et al. | | 5,746,754 A | 5/1998 | Chan |
| 5,601,571 A | 2/1997 | Moss | | 5,749,898 A | 5/1998 | Schulze et al. |
| 5,603,716 A | 2/1997 | Morgan et al. | | 5,755,729 A | 5/1998 | de la Torre et al. |
| 5,607,429 A | 3/1997 | Hayano et al. | | 5,755,791 A | 5/1998 | Whitson et al. |
| 5,618,290 A | 4/1997 | Toy et al. | | 5,766,176 A | 6/1998 | Duncan |
| 5,626,611 A | 5/1997 | Liu et al. | | 5,766,218 A | 6/1998 | Arnott |
| 5,626,614 A * | 5/1997 | Hart .................. 606/232 | | 5,766,250 A | 6/1998 | Chervitz et al. |
| 5,628,756 A | 5/1997 | Barker, Jr. et al. | | 5,769,894 A | 6/1998 | Ferragamo |

| | | | | | | |
|---|---|---|---|---|---|---|
| 5,769,899 A | 6/1998 | Schwartz et al. | | 5,968,047 A | 10/1999 | Reed |
| 5,772,673 A | 6/1998 | Cuny et al. | | 5,968,077 A | 10/1999 | Wojciechowicz et al. |
| 5,776,196 A | 7/1998 | Matsuzaki et al. | | 5,972,006 A | 10/1999 | Sciaino, Jr. |
| 5,782,845 A | 7/1998 | Shewchuk | | 5,976,125 A | 11/1999 | Graham |
| 5,782,862 A | 7/1998 | Bonutti | | 5,976,127 A | 11/1999 | Lax |
| 5,782,864 A | 7/1998 | Lizardi | | 5,980,524 A | 11/1999 | Justin et al. |
| 5,782,866 A | 7/1998 | Wenstrom, Jr. | | 5,980,539 A | 11/1999 | Kontos |
| 5,785,714 A | 7/1998 | Morgan et al. | | 5,980,558 A | 11/1999 | Wiley |
| 5,792,142 A | 8/1998 | Galitzer | | 5,980,559 A | 11/1999 | Bonutti |
| 5,792,149 A | 8/1998 | Sherts et al. | | 5,989,252 A | 11/1999 | Fumex |
| 5,796,127 A | 8/1998 | Hayafuji et al. | | 5,989,256 A | 11/1999 | Kuslich et al. |
| 5,797,915 A | 8/1998 | Pierson, III et al. | | 5,989,282 A | 11/1999 | Bonutti |
| 5,797,928 A | 8/1998 | Kogasaka | | 5,993,452 A | 11/1999 | Vandewalle |
| 5,800,407 A | 9/1998 | Eldor et al. | | 5,993,476 A | 11/1999 | Groiso |
| 5,810,824 A | 9/1998 | Chan | | 5,997,542 A | 12/1999 | Burke |
| 5,810,848 A | 9/1998 | Hayhurst | | 5,997,552 A | 12/1999 | Person et al. |
| 5,814,069 A | 9/1998 | Schulze et al. | | 5,997,575 A | 12/1999 | Whitson et al. |
| 5,814,070 A | 9/1998 | Borzone et al. | | 6,001,100 A | 12/1999 | Sherman et al. |
| 5,814,072 A | 9/1998 | Bonutti | | 6,007,538 A | 12/1999 | Levin |
| 5,814,073 A | 9/1998 | Bonutti | | 6,007,567 A | 12/1999 | Bonutti |
| 5,823,980 A | 10/1998 | Kopfer | | 6,010,525 A | 1/2000 | Bonutti et al. |
| 5,824,011 A | 10/1998 | Stone et al. | | 6,016,727 A | 1/2000 | Morgan |
| 5,830,234 A | 11/1998 | Wojciechowicz et al. | | 6,022,352 A | 2/2000 | Vandewalle |
| 5,843,084 A | 12/1998 | Hart et al. | | 6,022,373 A | 2/2000 | Li |
| 5,845,645 A | 12/1998 | Bonutti | | 6,024,758 A | 2/2000 | Thal |
| 5,846,254 A | 12/1998 | Schulze et al. | | 6,027,523 A | 2/2000 | Schmieding |
| 5,848,983 A | 12/1998 | Basaj et al. | | 6,030,410 A | 2/2000 | Zurbrugg |
| 5,849,012 A | 12/1998 | Abboudi | | 6,033,429 A | 3/2000 | Magovern |
| 5,860,973 A | 1/1999 | Michelson | | 6,033,430 A | 3/2000 | Bonutti |
| 5,868,740 A | 2/1999 | LeVeen et al. | | 6,039,753 A | 3/2000 | Meislin |
| 5,868,748 A | 2/1999 | Burke | | 6,041,485 A | 3/2000 | Pedlick et al. |
| 5,868,789 A | 2/1999 | Huebner | | 6,042,601 A | 3/2000 | Smith |
| 5,871,484 A | 2/1999 | Spievack et al. | | 6,045,551 A | 4/2000 | Bonutti |
| 5,871,486 A | 2/1999 | Huebner et al. | | 6,045,571 A | 4/2000 | Hill et al. |
| 5,871,490 A | 2/1999 | Schulze et al. | | 6,045,572 A | 4/2000 | Johnson et al. |
| 5,885,294 A | 3/1999 | Pedlick et al. | | 6,045,573 A | 4/2000 | Wenstrom, Jr. et al. |
| 5,891,168 A | 4/1999 | Thal | | 6,045,574 A | 4/2000 | Thal |
| 5,893,592 A | 4/1999 | Schulze et al. | | 6,047,826 A | 4/2000 | Kalinski et al. |
| 5,895,395 A | 4/1999 | Yeung | | 6,048,343 A | 4/2000 | Mathis et al. |
| 5,897,564 A | 4/1999 | Schulze et al. | | 6,051,006 A | 4/2000 | Shluzas et al. |
| 5,897,574 A | 4/1999 | Bonutti | | 6,051,007 A | 4/2000 | Hogendijk et al. |
| 5,899,902 A | 5/1999 | Brown et al. | | 6,053,916 A | 4/2000 | Moore |
| 5,899,938 A | 5/1999 | Sklar et al. | | 6,053,921 A | 4/2000 | Wagner et al. |
| 5,908,421 A | 6/1999 | Beger et al. | | 6,056,752 A | 5/2000 | Roger |
| 5,908,436 A | 6/1999 | Cuschieri et al. | | 6,056,772 A | 5/2000 | Bonutti |
| 5,910,148 A | 6/1999 | Reimels et al. | | 6,056,773 A | 5/2000 | Bonutti |
| 5,911,721 A | 6/1999 | Nicholson et al. | | 6,059,817 A | 5/2000 | Bonutti et al. |
| 5,918,604 A | 7/1999 | Whelan | | 6,059,818 A | 5/2000 | Johnson et al. |
| 5,921,986 A | 7/1999 | Bonutti | | 6,062,344 A | 5/2000 | Okabe et al. |
| 5,925,008 A | 7/1999 | Douglas | | 6,068,648 A | 5/2000 | Cole et al. |
| 5,928,231 A | 7/1999 | Klein et al. | | 6,071,305 A | 6/2000 | Brown et al. |
| 5,928,267 A | 7/1999 | Bonutti et al. | | 6,074,403 A | 6/2000 | Nord |
| RE36,289 E | 8/1999 | Le et al. | | 6,077,277 A | 6/2000 | Mollenauer et al. |
| 5,931,838 A | 8/1999 | Vito | | 6,077,292 A | 6/2000 | Bonutti |
| 5,931,844 A | 8/1999 | Thompson et al. | | 6,080,185 A | 6/2000 | Johnson et al. |
| 5,931,869 A | 8/1999 | Boucher et al. | | 6,086,591 A | 7/2000 | Bojarski |
| 5,935,119 A | 8/1999 | Guy et al. | | 6,086,592 A | 7/2000 | Rosenberg et al. |
| 5,935,133 A | 8/1999 | Wagner et al. | | 6,086,608 A | 7/2000 | Ek et al. |
| 5,935,149 A | 8/1999 | Ek | | 6,093,200 A | 7/2000 | Liu et al. |
| 5,938,668 A | 8/1999 | Scirica et al. | | 6,096,060 A | 8/2000 | Fitts et al. |
| 5,941,439 A | 8/1999 | Kammerer et al. | | 6,099,527 A | 8/2000 | Hochschuler et al. |
| 5,941,900 A | 8/1999 | Bonutti | | 6,099,530 A | 8/2000 | Simonian et al. |
| 5,944,739 A | 8/1999 | Zlock et al. | | 6,099,568 A | 8/2000 | Simonian et al. |
| 5,946,783 A | 9/1999 | Plociennik et al. | | 6,106,545 A | 8/2000 | Egan |
| 5,947,915 A | 9/1999 | Thibodo, Jr. | | 6,110,128 A | 8/2000 | Andelin et al. |
| 5,947,982 A | 9/1999 | Duran | | 6,117,160 A | 9/2000 | Bonutti |
| 5,947,999 A | 9/1999 | Groiso | | 6,117,162 A | 9/2000 | Schmieding et al. |
| 5,948,002 A | 9/1999 | Bonutti | | 6,123,710 A | 9/2000 | Pinczewski et al. |
| 5,951,559 A | 9/1999 | Burkhart | | 6,132,433 A | 10/2000 | Whelan |
| 5,951,560 A | 9/1999 | Simon et al. | | 6,132,437 A | 10/2000 | Omurtag et al. |
| 5,954,747 A | 9/1999 | Clark | | 6,139,565 A | 10/2000 | Stone et al. |
| 5,957,953 A | 9/1999 | DiPoto et al. | | RE36,974 E * | 11/2000 | Bonutti ............... 606/232 |
| 5,961,521 A | 10/1999 | Roger et al. | | 6,143,017 A | 11/2000 | Thal |
| 5,961,524 A | 10/1999 | Crombie | | 6,146,406 A | 11/2000 | Shluzas et al. |
| 5,964,764 A | 10/1999 | West, Jr. et al. | | 6,146,408 A | 11/2000 | Bartlett |
| 5,964,767 A | 10/1999 | Tapia et al. | | 6,149,653 A | 11/2000 | Deslauriers |
| 5,964,769 A | 10/1999 | Wagner et al. | | 6,149,669 A * | 11/2000 | Li ............... 606/232 |
| 5,964,783 A | 10/1999 | Grafton et al. | | 6,152,928 A | 11/2000 | Wenstrom, Jr. |
| 5,968,045 A | 10/1999 | Frazier | | 6,152,934 A | 11/2000 | Harper et al. |

| | | | | | | |
|---|---|---|---|---|---|---|
| 6,152,936 | A | 11/2000 | Christy et al. | 6,447,516 | B1 | 9/2002 | Bonutti |
| 6,152,949 | A | 11/2000 | Bonutti | 6,451,030 | B1 | 9/2002 | Li et al. |
| 6,156,039 | A | 12/2000 | Thal | 6,454,768 | B1 | 9/2002 | Jackson |
| 6,156,056 | A | 12/2000 | Kearns et al. | 6,458,134 | B1 | 10/2002 | Songer et al. |
| 6,159,234 | A | 12/2000 | Bonutti et al. | 6,461,373 | B2 | 10/2002 | Wyman et al. |
| 6,165,203 | A | 12/2000 | Krebs | 6,464,713 | B2 | 10/2002 | Bonutti |
| 6,168,598 | B1 | 1/2001 | Martello | 6,468,293 | B2 | 10/2002 | Bonutti et al. |
| 6,168,628 | B1 | 1/2001 | Huebner | 6,471,707 | B1 | 10/2002 | Miller et al. |
| 6,179,840 | B1 | 1/2001 | Bowman | 6,475,230 | B1 | 11/2002 | Bonutti et al. |
| 6,183,461 | B1 | 2/2001 | Matsuura et al. | 6,482,210 | B1 | 11/2002 | Skiba et al. |
| 6,187,025 | B1 | 2/2001 | Machek | 6,485,504 | B1 | 11/2002 | Johnson et al. |
| 6,190,401 | B1 * | 2/2001 | Green et al. ............... 606/224 | 6,497,901 | B1 | 12/2002 | Royer |
| 6,190,411 | B1 | 2/2001 | Lo et al. | 6,500,184 | B1 | 12/2002 | Chan et al. |
| 6,193,754 | B1 | 2/2001 | Seedhom | 6,500,195 | B2 | 12/2002 | Bonutti |
| 6,200,318 | B1 | 3/2001 | Har-Shai et al. | RE37,963 | E | 1/2003 | Thal |
| 6,200,329 | B1 | 3/2001 | Fung et al. | 6,503,267 | B2 | 1/2003 | Bonutti et al. |
| 6,200,330 | B1 | 3/2001 | Benderev et al. | 6,506,190 | B1 * | 1/2003 | Walshe ................. 606/139 |
| 6,203,556 | B1 | 3/2001 | Evans et al. | 6,508,820 | B2 | 1/2003 | Bales |
| 6,203,565 | B1 | 3/2001 | Bonutti et al. | 6,508,821 | B1 | 1/2003 | Schwartz et al. |
| 6,203,572 | B1 | 3/2001 | Johnson et al. | 6,508,830 | B2 | 1/2003 | Steiner |
| 6,206,883 | B1 | 3/2001 | Tunc | 6,511,498 | B1 | 1/2003 | Fumex |
| 6,210,376 | B1 | 4/2001 | Grayson | 6,511,499 | B2 | 1/2003 | Schmieding et al. |
| 6,214,012 | B1 | 4/2001 | Karpman et al. | 6,517,542 | B1 | 2/2003 | Papay et al. |
| 6,217,580 | B1 | 4/2001 | Levin | 6,517,552 | B1 | 2/2003 | Nord et al. |
| 6,221,107 | B1 | 4/2001 | Steiner et al. | 6,517,578 | B2 | 2/2003 | Hein |
| 6,228,096 | B1 | 5/2001 | Marchand | 6,517,579 | B1 | 2/2003 | Paulos et al. |
| 6,231,592 | B1 | 5/2001 | Bonutti et al. | 6,520,964 | B2 | 2/2003 | Tallarida et al. |
| 6,235,057 | B1 | 5/2001 | Roger et al. | 6,520,980 | B1 | 2/2003 | Foerster |
| 6,238,395 | B1 | 5/2001 | Bonutti | 6,524,317 | B1 | 2/2003 | Ritchart et al. |
| 6,241,734 | B1 | 6/2001 | Scribner et al. | 6,527,777 | B2 | 3/2003 | Justin |
| 6,241,747 | B1 | 6/2001 | Ruff | 6,527,794 | B1 | 3/2003 | McDevitt et al. |
| 6,241,771 | B1 | 6/2001 | Gresser et al. | 6,527,795 | B1 | 3/2003 | Lizardi |
| 6,245,081 | B1 | 6/2001 | Bowman et al. | 6,533,795 | B1 | 3/2003 | Tran et al. |
| 6,258,091 | B1 | 7/2001 | Sevrain et al. | 6,533,802 | B2 | 3/2003 | Bojarski et al. |
| 6,267,766 | B1 | 7/2001 | Burkhart | 6,537,319 | B2 | 3/2003 | Whelan |
| 6,269,716 | B1 | 8/2001 | Amis | 6,540,750 | B2 | 4/2003 | Burkhart |
| 6,270,518 | B1 | 8/2001 | Pedlick et al. | 6,540,769 | B1 | 4/2003 | Miller, III |
| 6,273,890 | B1 | 8/2001 | Frazier | 6,540,770 | B1 | 4/2003 | Tornier et al. |
| 6,283,973 | B1 | 9/2001 | Hubbard et al. | 6,544,281 | B2 | 4/2003 | ElAttrache et al. |
| 6,283,996 | B1 | 9/2001 | Chervitz et al. | 6,547,564 | B1 | 4/2003 | Hansson |
| 6,287,307 | B1 | 9/2001 | Abboudi | 6,547,778 | B1 | 4/2003 | Sklar et al. |
| 6,287,325 | B1 | 9/2001 | Bonutti | 6,547,800 | B2 | 4/2003 | Foerster et al. |
| 6,293,961 | B2 | 9/2001 | Schwartz et al. | 6,551,330 | B1 | 4/2003 | Bain et al. |
| 6,296,659 | B1 | 10/2001 | Foerster | 6,551,343 | B1 | 4/2003 | Tormala et al. |
| 6,299,615 | B1 | 10/2001 | Huebner | 6,553,802 | B1 | 4/2003 | Jacob |
| 6,302,888 | B1 | 10/2001 | Mellinger et al. | 6,554,830 | B1 | 4/2003 | Chappius |
| 6,302,899 | B1 | 10/2001 | Johnson et al. | 6,554,852 | B1 | 4/2003 | Oberlander |
| 6,306,156 | B1 | 10/2001 | Clark | 6,554,862 | B2 | 4/2003 | Hays et al. |
| 6,306,159 | B1 | 10/2001 | Schwartz et al. | 6,562,071 | B2 | 5/2003 | Jarvinen et al. |
| 6,309,405 | B1 | 10/2001 | Bonutti | 6,565,572 | B2 | 5/2003 | Chappius |
| 6,312,448 | B1 | 11/2001 | Bonutti | 6,565,573 | B1 | 5/2003 | Ferrante et al. |
| 6,315,788 | B1 | 11/2001 | Roby | 6,569,186 | B1 | 5/2003 | Winters et al. |
| 6,319,271 | B1 | 11/2001 | Schwartz et al. | 6,569,187 | B1 | 5/2003 | Bonutti et al. |
| 6,328,758 | B1 | 12/2001 | Tornier et al. | 6,572,635 | B1 | 6/2003 | Bonutti |
| 6,342,060 | B1 | 1/2002 | Adams | 6,575,925 | B1 | 6/2003 | Noble |
| 6,343,531 | B2 | 2/2002 | Amis | 6,579,295 | B1 | 6/2003 | Supinski |
| 6,358,270 | B1 | 3/2002 | Lemer | 6,582,453 | B1 | 6/2003 | Tran et al. |
| 6,364,897 | B1 | 4/2002 | Bonutti | 6,585,730 | B1 | 7/2003 | Foerster |
| 6,368,322 | B1 | 4/2002 | Luks et al. | 6,585,740 | B2 | 7/2003 | Schlapfer et al. |
| 6,368,326 | B1 | 4/2002 | Dakin et al. | 6,585,750 | B2 | 7/2003 | Bonutti et al. |
| 6,368,343 | B1 | 4/2002 | Bonutti et al. | 6,589,245 | B1 | 7/2003 | Weiler et al. |
| 6,371,124 | B1 | 4/2002 | Whelan | 6,589,246 | B1 | 7/2003 | Hack et al. |
| 6,379,361 | B1 | 4/2002 | Beck, Jr. et al. | 6,592,609 | B1 | 7/2003 | Bonutti |
| 6,383,190 | B1 | 5/2002 | Preissman | 6,595,911 | B2 | 7/2003 | LoVuolo |
| 6,383,199 | B2 | 5/2002 | Carter et al. | 6,599,289 | B1 | 7/2003 | Bojarski et al. |
| 6,387,113 | B1 | 5/2002 | Hawkins et al. | 6,599,319 | B2 | 7/2003 | Knudsen et al. |
| 6,387,129 | B2 | 5/2002 | Rieser et al. | 6,605,096 | B1 | 8/2003 | Ritchart |
| 6,391,030 | B1 | 5/2002 | Wagner et al. | 6,607,548 | B2 | 8/2003 | Pohjonen et al. |
| 6,398,785 | B2 | 6/2002 | Carchidi et al. | 6,610,079 | B1 | 8/2003 | Li et al. |
| 6,406,479 | B1 | 6/2002 | Justin et al. | 6,613,018 | B2 | 9/2003 | Bagga et al. |
| 6,409,743 | B1 | 6/2002 | Fenton, Jr. | 6,616,694 | B1 | 9/2003 | Hart |
| 6,413,260 | B1 | 7/2002 | Berrevoets et al. | 6,620,166 | B1 | 9/2003 | Wenstrom, Jr. et al. |
| 6,423,088 | B1 | 7/2002 | Fenton, Jr. | 6,620,185 | B1 | 9/2003 | Harvie et al. |
| 6,428,562 | B2 | 8/2002 | Bonutti | 6,620,195 | B2 | 9/2003 | Goble et al. |
| 6,432,123 | B2 | 8/2002 | Schwartz et al. | 6,620,329 | B2 | 9/2003 | Rosen et al. |
| 6,436,123 | B1 | 8/2002 | Magovern | 6,620,349 | B1 | 9/2003 | Lopez |
| 6,436,124 | B1 | 8/2002 | Anderson et al. | 6,623,492 | B1 | 9/2003 | Berube et al. |
| 6,440,134 | B1 | 8/2002 | Zaccherotti et al. | 6,623,524 | B2 | 9/2003 | Schmieding |
| 6,440,136 | B1 | 8/2002 | Gambale et al. | 6,626,910 | B1 | 9/2003 | Hugues et al. |

| | | |
|---|---|---|
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B1 | 10/2003 | Plouhar et al. |
| 6,641,596 B1 * | 11/2003 | Lizardi ........................ 606/232 |
| 6,641,597 B2 | 11/2003 | Burkhart et al. |
| 6,645,227 B2 | 11/2003 | Fallin et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,001,429 B2 | 2/2006 | Ferguson |
| 7,004,959 B2 * | 2/2006 | Bonutti ........................ 606/232 |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |
| 7,201,722 B2 | 4/2007 | Krueger |
| 7,255,675 B2 | 8/2007 | Gertner et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,513,910 B2 | 4/2009 | Buskirk et al. |
| 7,578,825 B2 | 8/2009 | Huebner |
| 7,585,311 B2 | 9/2009 | Green et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,632,287 B2 | 12/2009 | Baker et al. |
| 7,651,509 B2 | 1/2010 | Bojarski et al. |
| 7,658,750 B2 * | 2/2010 | Li ................................ 606/232 |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 7,776,041 B1 | 8/2010 | Walters |
| 7,819,895 B2 | 10/2010 | Ginn et al. |
| 7,875,058 B2 | 1/2011 | Holmes, Jr. |
| 7,981,140 B2 | 7/2011 | Burkhart |
| 8,062,334 B2 | 11/2011 | Green et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0037131 A1 | 11/2001 | Schmieding et al. |
| 2001/0037153 A1 | 11/2001 | Rockwood et al. |
| 2001/0041916 A1 * | 11/2001 | Bonutti ........................ 606/232 |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 * | 2/2002 | Sikora et al. .................. 606/232 |
| 2002/0029066 A1 | 3/2002 | Foerster |

| Publication No. | Date | Inventor |
|---|---|---|
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1* | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1* | 12/2002 | Bonutti ............ 606/232 |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1* | 6/2003 | Eichhorn et al. ............ 606/232 |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1* | 9/2003 | Oberlander ............ 606/232 |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1* | 1/2004 | Fallin et al. ............ 606/232 |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1* | 5/2004 | Sinnott et al. ............ 606/232 |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1* | 7/2004 | Shelton et al. ............ 606/151 |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |

| | | |
|---|---|---|
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1* | 2/2006 | Yeung et al. ............... 606/232 |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0229671 A1 | 10/2006 | Steiner et al. |
| 2006/0235407 A1 | 10/2006 | Wang et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0280768 A1 | 12/2006 | Hwang et al. |
| 2006/0282082 A1 | 12/2006 | Fanton et al. |
| 2006/0282085 A1 | 12/2006 | Stone et al. |
| 2006/0293709 A1* | 12/2006 | Bojarski et al. ............... 606/232 |
| 2007/0005080 A1 | 1/2007 | Wolniewicz et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1* | 5/2007 | Deffenbaugh et al. ....... 606/104 |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0248091 A1 | 10/2009 | Teague et al. |
| 2009/0265014 A1 | 10/2009 | May et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1* | 2/2010 | Schaffhausen ............... 606/139 |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |

| | | |
|---|---|---|
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0197271 A1 | 8/2012 | Astorino et al. |

FOREIGN PATENT DOCUMENTS

| | | |
|---|---|---|
| AU | 440266 | 10/1967 |
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2008002550 A2 | 1/2008 |
| WO | WO-2009012021 A1 | 1/2009 |

OTHER PUBLICATIONS

"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

"Make your next tendon repair an open-and-shut case. The Teno Fix® Tendon Repair System", Teno Fix® brochure, 2003 (2 pages) Ortheon® Medical.

"PANALOK Anchor with PDS II and ETHIBOND Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-Journal 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.

Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

"Arthroscopic Meniscal Repair using the Meniscal Cinch™ ", Surgical Technique brochure. (2008) Arthrex® 6 sheets.

Pioneer® Sternal Cable System (2010).

Rapid Sternal Closure (2006) KLS Martin L.P. http://www.rapidsternalclosure.com/medical/demo.php Web accessed Sep. 8, 2008.

Saxena, Pankaj, MCh, DNB et al., "Use of Double Wires in Sternal Closure, A Useful Technique," Texas Heart® Institute. Journal List>Tex Heart Inst J > v.33(4); (2006).

Zeitani, Jacob, M.D., "A New Sternal Reinforcement Device to Prevent and Treat Sternal Dehiscence," CTSNet.org (Jun. 30, 2008).

Arthrotek, A Biomet Company; Knees; Sure fire Hybrid Meniscal Device. (2005).

Invitation to Pay Additional Fees mailed Jul. 19, 2012, for PCT/US2012/037703 claiming benefit of U.S. Appl. No. 13/109,667, filed May 7, 2011.

US 6,238,418, 05/2001, Schwartz et al. (withdrawn)

* cited by examiner

SOFT TISSUE REPAIR DEVICE AND ASSOCIATED METHODS

CROSS-REFERENCE TO RELATED APPLICATIONS

This application is a divisional of U.S. patent application Ser. No. 12/014,399, filed on Jan. 15, 2008, now U.S. Pat. No. 7,909,851, issued on Mar. 22, 2011, which claims the benefit of U.S. Provisional Application No. 60/885062, filed on Jan. 6, 2007, and of U.S. Provisional Application No. 60/885057, filed on Jan. 16, 2007, and which is a continuation-in-part of the following applications:

U.S. patent application Ser. No. 11/347,661 filed on Feb. 3, 2006, now U.S. Pat. No. 7,749,250, issued on Jul. 6, 2010;

U.S. patent application No. 11/935681 filed on Nov. 6, 2007, now U.S. Pat. No. 7,905,903, issued on Mar. 15, 2011;

U.S. patent application Ser. No. 11/869,440 filed on Oct. 9, 2007, now U.S. Pat. No. 7,857,830, issued on Dec. 28, 2010, which is a continuation-in-part of U.S. patent application Ser. No. 11/408,282, filed on Apr. 20, 2006.now abandoned; and U.S. patent application Ser. No. 11/541,506, filed on Sep. 29, 2006, now U.S. Pat. No. 7,601,165, issued on Oct. 13, 2009.

The disclosures of the above applications are incorporated herein by reference.

INTRODUCTION

Tears or other defects caused by trauma or disease in soft tissue, such as cartilage, ligament, or muscle, can be repaired by suturing. Various repair devices have been developed for facilitating suturing and are effective for their intended purposes. Nevertheless, tissue repair devices for facilitating suturing are still desirable.

SUMMARY

The present teachings provide a soft tissue repair device. The device can include an inserter having a distal portion, first and second anchors carried externally onto the distal portion, and a flexible strand coupling the first and second anchors and forming an adjustable knotless loop.

In one aspect, each of the first and second anchors is a flexible sleeve having first and second ends and an internal passage between the first and second ends. In another aspect, each of the first and second anchors is substantially rigid having first and second ends and an internal passage between the first and second ends.

The present teachings also provide a method for repairing a tear in a meniscus during arthroscopic knee procedure. The method includes coupling first and second anchors with a flexible strand, forming an adjustable knotless loop with the flexible strand, and loading the first and second anchors coupled with the adjustable knotless loop on an external surface of an inserter. The method further includes inserting the inserter through the tear to an outer surface of the meniscus, sequentially deploying the first and second anchors from the inserter on an outer surface of the meniscus, self-locking the adjustable loop, and reducing the tear.

The present teachings further provide a method for repairing a defect in a fibrous soft tissue includes passing a distal portion of an inserter through corresponding longitudinal bores of first and second anchors. The method includes coupling the first and second anchors with a flexible strand, and forming an adjustable knotless loop with the flexible strand.

In some embodiments, the method includes inserting a distal portion of an inserter through a defect of the fibrous soft tissue to an outer surface of the fibrous soft tissue and expelling first and second tubular anchors from the distal portion of the inserter at first and second locations on an outer surface of the fibrous soft tissue. The distal portion of the inserter passes through corresponding longitudinal bores of the first and second tubular anchor. The method includes tensioning a flexible strand that couples the first and second anchors such that an adjustable loop formed by the flexible strand self-locks and reduces the defect.

In some embodiments, a deploying member is moved along a channel of the inserter to expel the first and second anchors sequentially. The deploying member includes a projection that can be deformed elastically when the deploying member is retracted through the longitudinal bore of the second anchor after the first anchor is deployed.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, although the present teachings are illustrated in an application for meniscus repair in knee surgery, the present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone.

Figure 1:
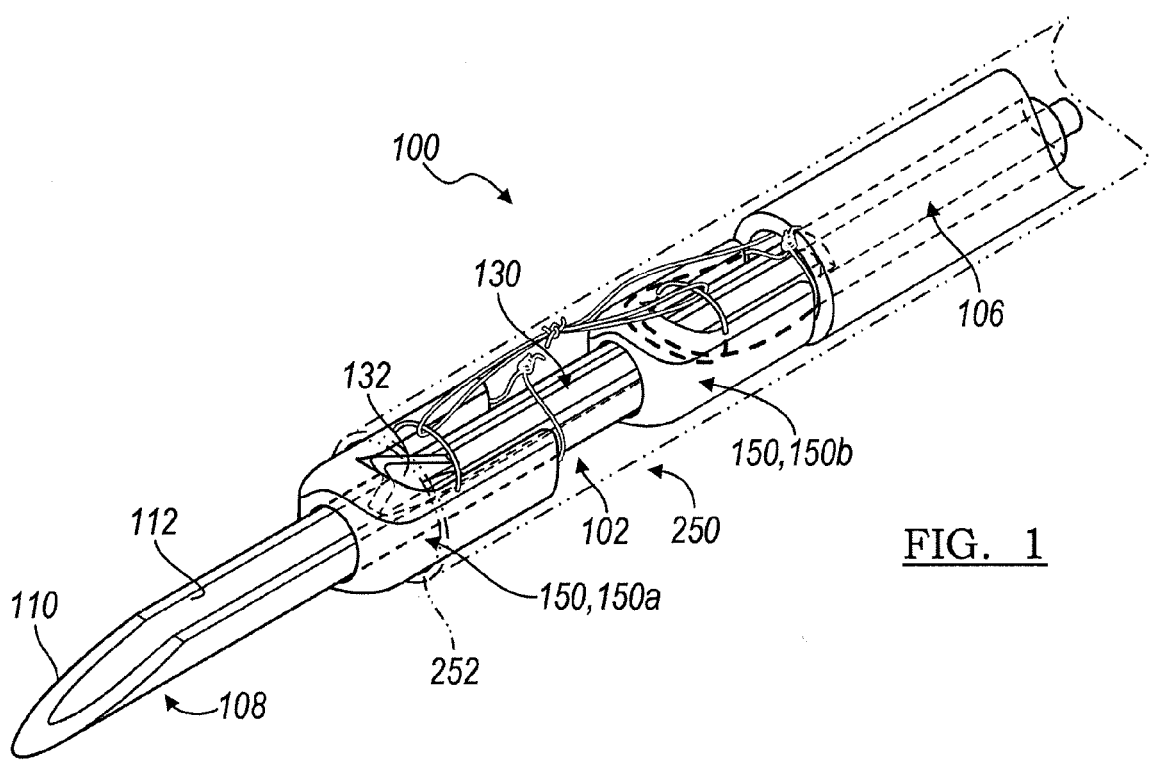
FIG. 1 is a perspective view of a tissue repair device according to the present teachings shown in a first configuration.

An exemplary tissue repair device 100 according to the present teachings is illustrated in FIG. 1. The device 100 can include an inserter 102, a stop member or shaft 106 and a depth limiting device 250, such as a plastic tube that can be cut to desired length. The inserter 102 can be externally pre-loaded on its outer surface with one or more flexible anchors 150. Two anchors 150 are illustrated in FIG. 1 and are referenced hereinafter as first and second anchors 150a, 150b, if desirable for further clarity. The letters "a" and "b" will also be appended to distinguish corresponding features of the first and second anchors 150a, 150b, if desirable for clarity. The inserter 102 can include a distal portion 108 defining an inclined sharp edge 110. The inserter 102 can define an open longitudinal channel 112. An anchor deploying member 130 can be slidably received in the channel 112 for deploying the anchors 150 off the inserter 102. The shaft 106 can be solid or hollow, and can operate as a stop member for the anchors 150a, 150b, which are not loaded in or within the longitudinal channel 112 as in prior art devices, but are instead carried externally and completely outside the distal portion 108 of the inserter 102, with no portion of the anchors 150 received within the longitudinal channel 112, as described below.

Figure 1A:
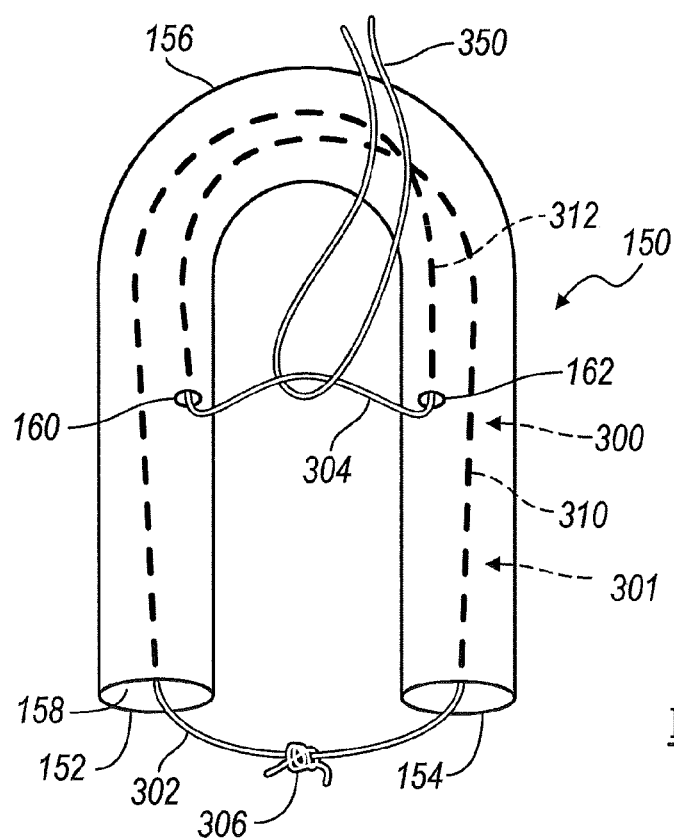
FIG. 1A is a perspective view of a flexible anchor according to the present teachings.
Figure 2:
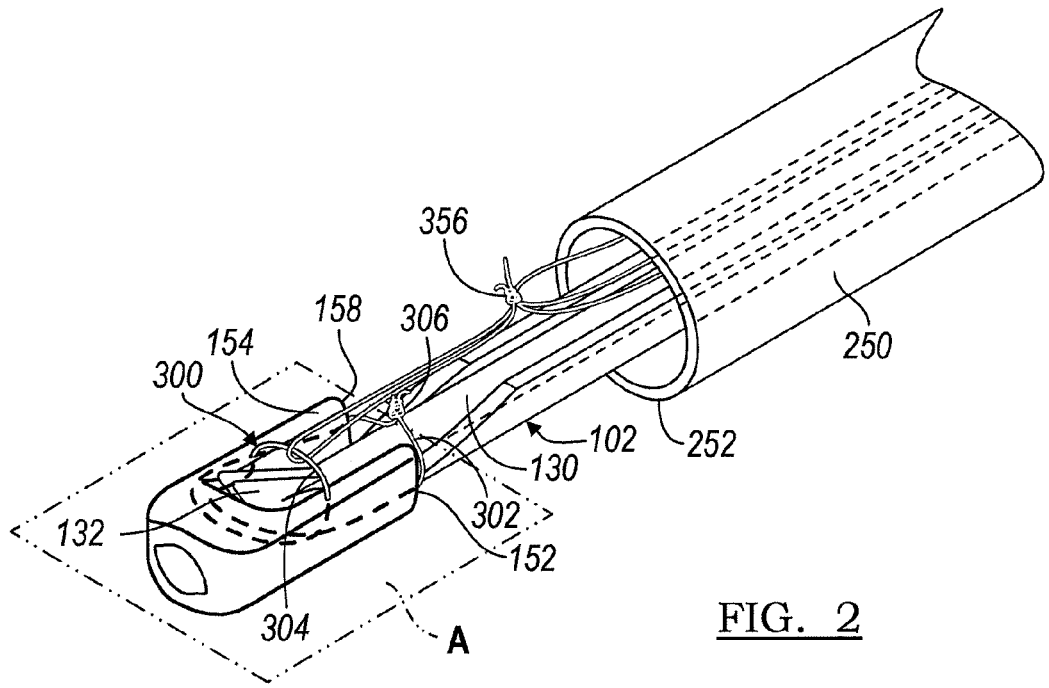
FIG. 2 is a perspective view of the device of FIG. 1, shown in a second configuration.

Referring to FIGS. 1, 1A and 2, each flexible anchor 150 can be an elongated member having first and second ends 152, 154. The first and second ends 152, 154 are blunt and substantially perpendicular to the longitudinal axis of the anchor 150. The flexible anchor 150 can be made of resorbable or non-resorbable materials, including braided suture, sponges and sponge-like materials in solid form, perforated materials, woven/braided from biocompatible materials or fibers, such as, for example, polymer, polyester, polyethylene, cotton, silk, or other natural or synthetic materials, including sponges and sponge-like materials. The flexible anchor 150 can also be an elongated tubular or solid member or a two-dimensional member with or without internal bores. The flexible anchor 150 can have any properties that allow the flexible anchor 150 to change shape. The flexible anchor 150 can be, for example, compliant, flexible, foldable, squashable, squeezable, deformable, limp, flaccid, elastic, low-modulus, soft, spongy, perforated or any other flexible member which can change shape. In some aspects, the flexible anchor 150 can be coated with biological or biocompatible coatings, and it can also be soaked in platelets and other biologics, which can be easily absorbed by the flexible anchor 150 in particular when, for example, the flexible anchor 150 is made from spongy, absorbent material.

It should be understood by the above description that the flexible anchor 150 cannot pierce or otherwise penetrate tissue either with the first and second ends 152, 154, which are blunt or with any other portion thereof. The flexible anchor 150 can be loaded solely on the exterior of the distal portion 108 of the inserter 102 in a folded configuration, such that the first and second ends 152, 154 are facing each other. Accordingly, no portion of the flexible anchor 150 is received even partially in or within the inserter 102 or the channel 112, in contrast to prior art devices in which one or more anchors are substantially received within hollow tubular inserters or hollow needles. More specifically, an intermediate portion 156 of the flexible anchor 150 can be pierced through by the sharp edge 110 of the inserter 102, such that the first and second ends 152, 154 extend opposing one another along the proximal portion 108 of the inserter 102, as shown in FIG. 1. The flexible anchor 150 can be in the form of an elongate flexible tube defining a bore 158 along its length, as shown in FIG. 1A. The flexible anchor 150 can be formed of suture braided without a core.

Figure 6:
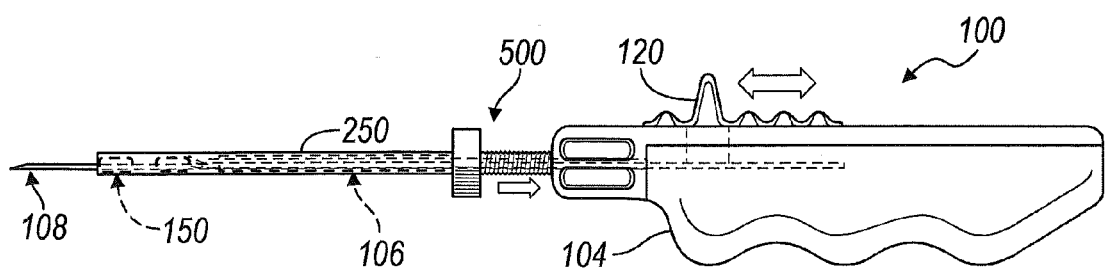
FIG. 6 is a perspective view of a tissue repair device according to the present teachings.
Figure 7:
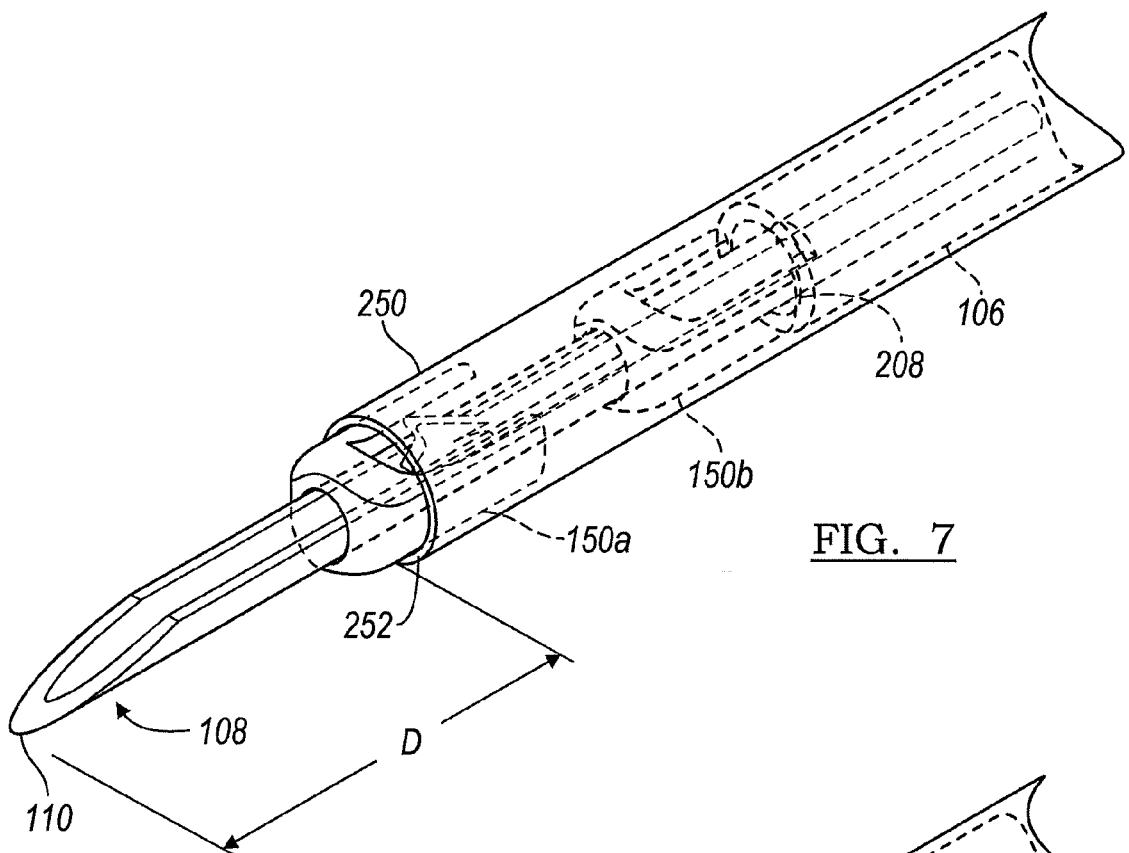
FIG. 7 is an enlarged side view of the device of FIG. 6, shown with a depth limiting device in a first position.
Figure 8:
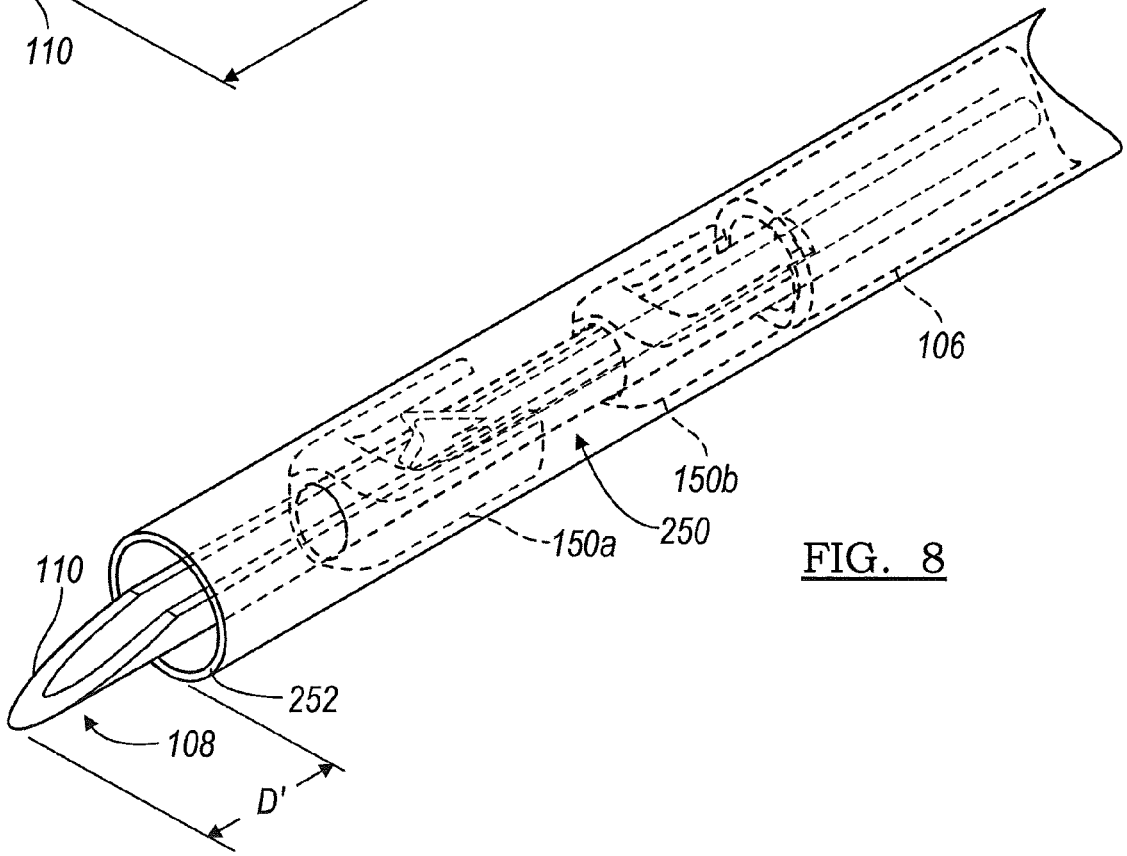
FIG. 8 is an enlarged side view of the device of FIG. 6, shown with a depth limiting device in a second position.

Referring to FIGS. 6-8 the device 100 can include an adjustment actuator 500 for the depth limiting device 250. The actuator 500 can be, for example, a rack-and-gear mechanism for moving the inserter 102 relative to the depth limiting device 250 between the position shown in FIG. 7, in which the inserter 102 extends a distance "D" beyond a distal end 252 of the depth limiting device 250, and the position of FIG. 8, in which the inserter 102 extends a distance "D'" beyond the distal end 252 of the depth limiting device 250. The depth limiting device 250 can be in the form of a transparent plastic tube.

Figure 16:
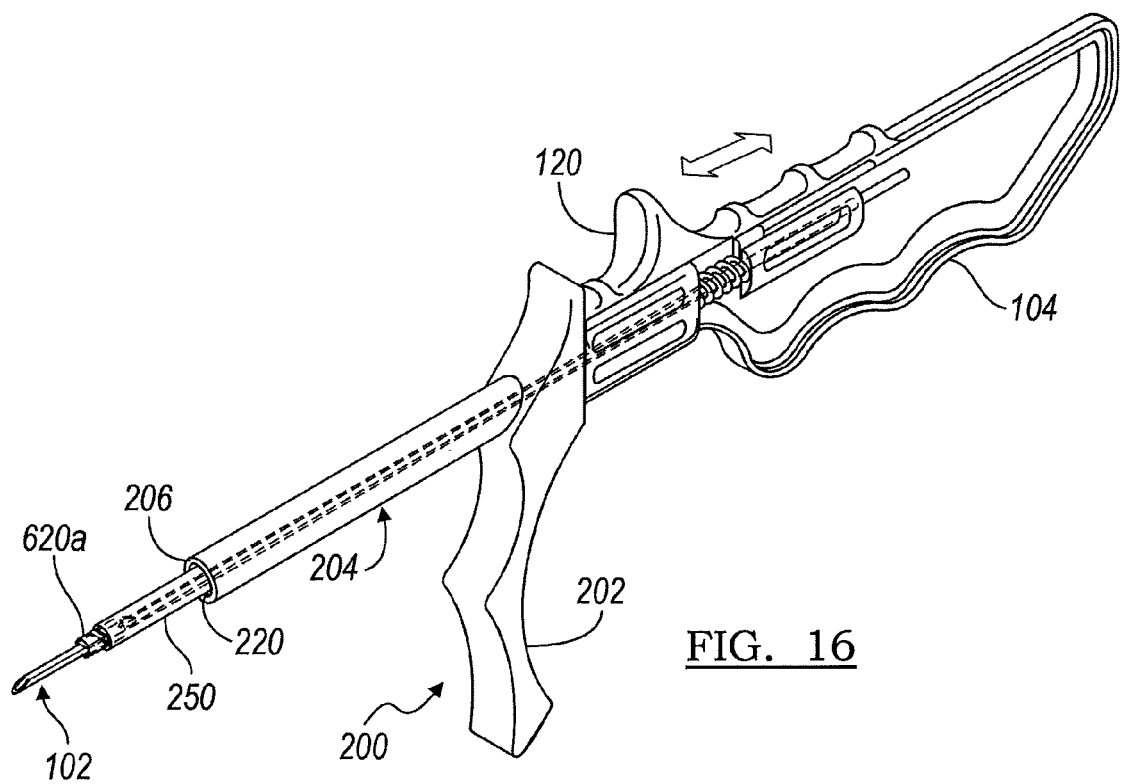
FIG. 16 is a perspective view of a tissue repair device according to the present teachings.
Figure 16A:
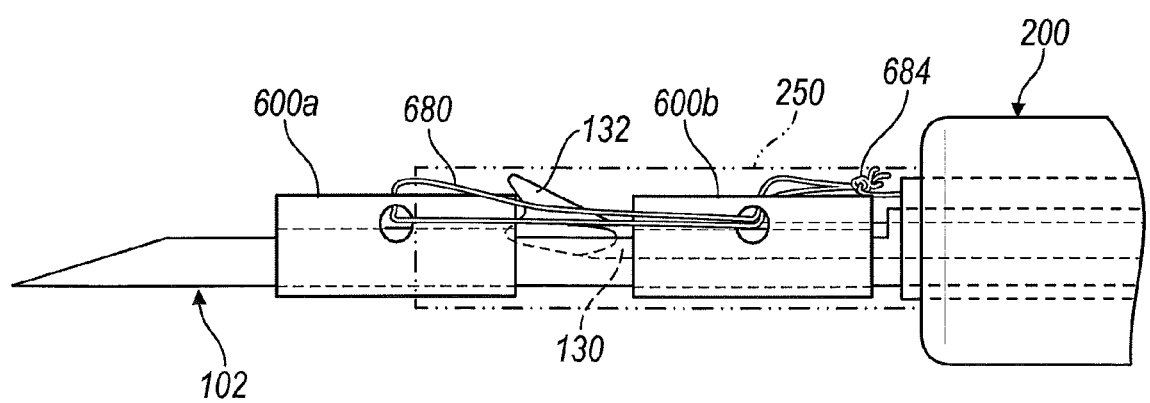
FIG. 16A is an enlarged side view of the device of FIG. 16.
Figure 17:
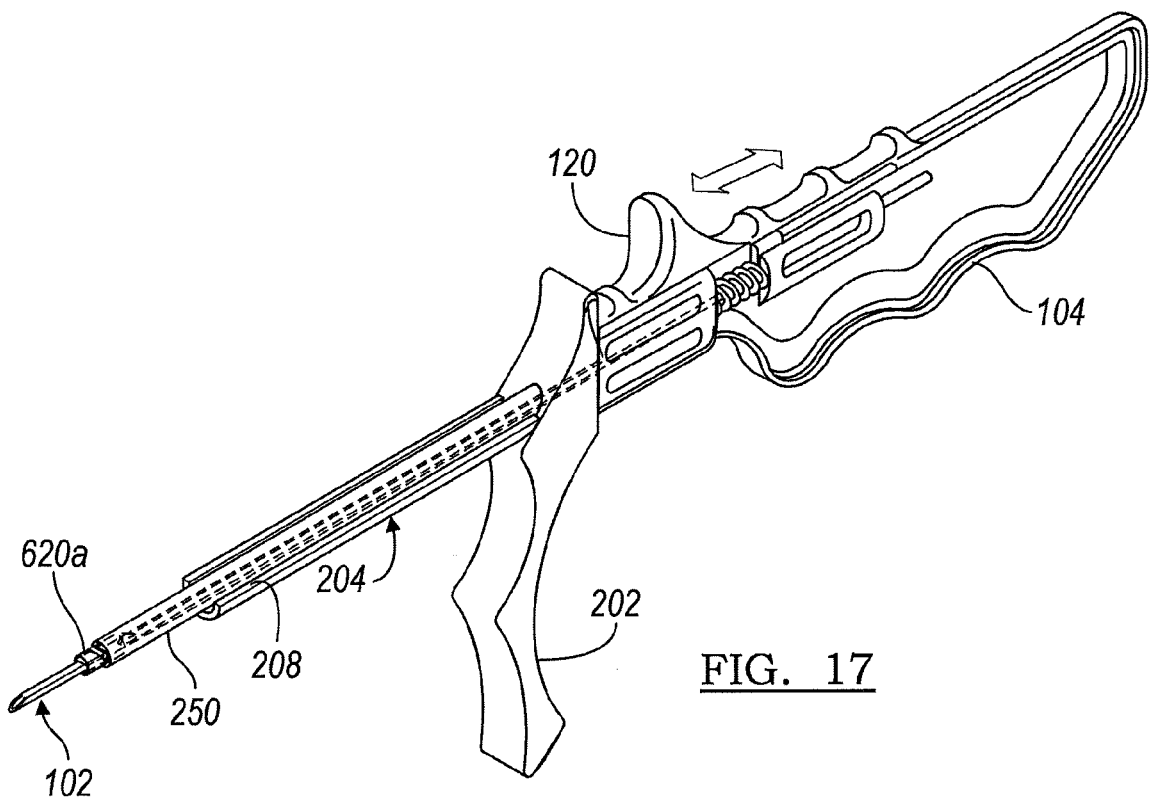
FIG. 17 is a perspective view of a tissue repair device according to the present teachings.
Figure 17A:
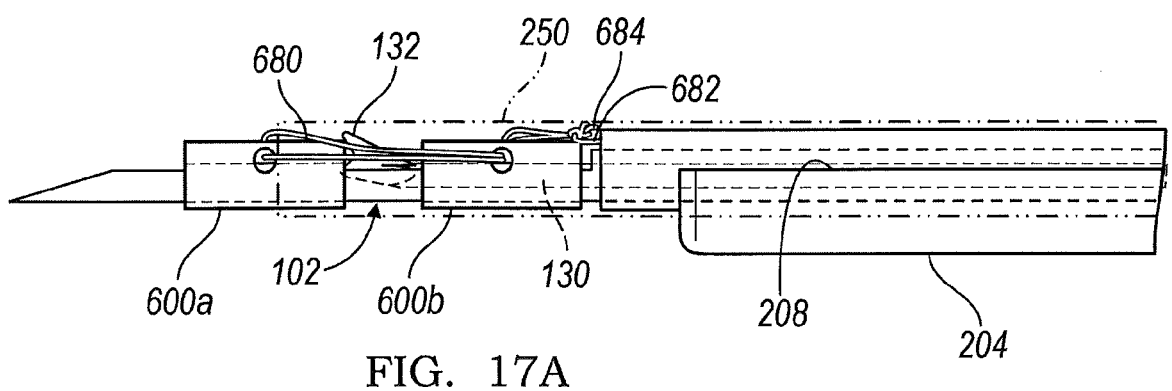
FIG. 17A is an enlarged side view of the device of FIG. 17.

The inserter 102 can be used with a cannula 200, shown in FIG. 16. The cannula 200 can include a handle 202 and a tubular or hollow shaft 204. The shaft 204 of the cannula 200 can have a longitudinal bore 220 having an inner diameter sized to receive the inserter 102. The shaft 204 of the cannula 200 can have a distal end 206 which can be perpendicular relative to the shaft 204, as shown in FIG. 16, but can also be slanted relative to the shaft 204. The distal end 206 has a rounded, blunt or smooth edge not intended to or capable of piercing or otherwise penetrating tissue. The cannula shaft 204 can include a cut-away slot 208 defining a viewing window 210, as shown in FIG. 17.

Referring to FIG. 1A, the flexible anchor 150 can be assembled bent in a U-shape form on the inserter 102 with a continuous strand loop 300 attached thereon. The strand loop 300 can be formed by a single segment of flexible strand 301 passing through the bore 158 of the anchor 150, such that the strand loop 300 includes a first external segment or portion 302 outside the bore 158 and between the ends 152, 154, and a second external segment portion 304 located outside the bore 158 and exiting the bore 158 from exit openings 160, 162 on opposite sides of the bent U-shape of the flexible anchor 150. The flexible strand 301 can be made of braided filaments or fibers of biocompatible material, including natural and synthetic fibers, such as cotton, silk, polymer, polyester, polyethylene, thin wire, suture, and other materials.

The strand loop 300 can be formed by tying the ends of the segment with a knot 306 which can be positioned on either the first external portion 302 or the second external portion 304. It will be appreciated that the loop 300 can define first and second secondary loops or sub-loops 310, 312. The first sub-loop 310 can include the first external portion 302, and the second sub-loop can include the second external portion 304. The first and second sub-loops 310, 312 can intersect each other, and each sub-loop 310, 312 can pass through the bent portion of the bore 158 corresponding to the intermediate portion 156 of the flexible anchor 150.

Figure 3:
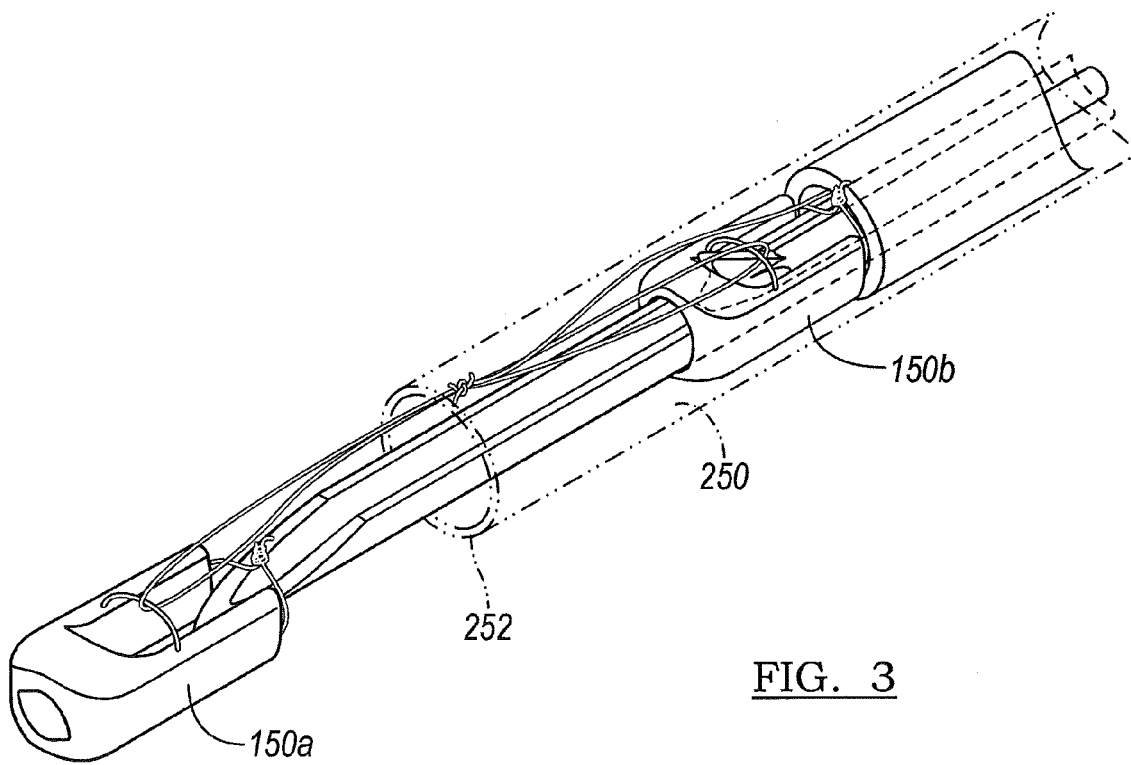
FIG. 3 is a perspective view of the device of FIG. 1, shown in a third configuration.
Figure 4:
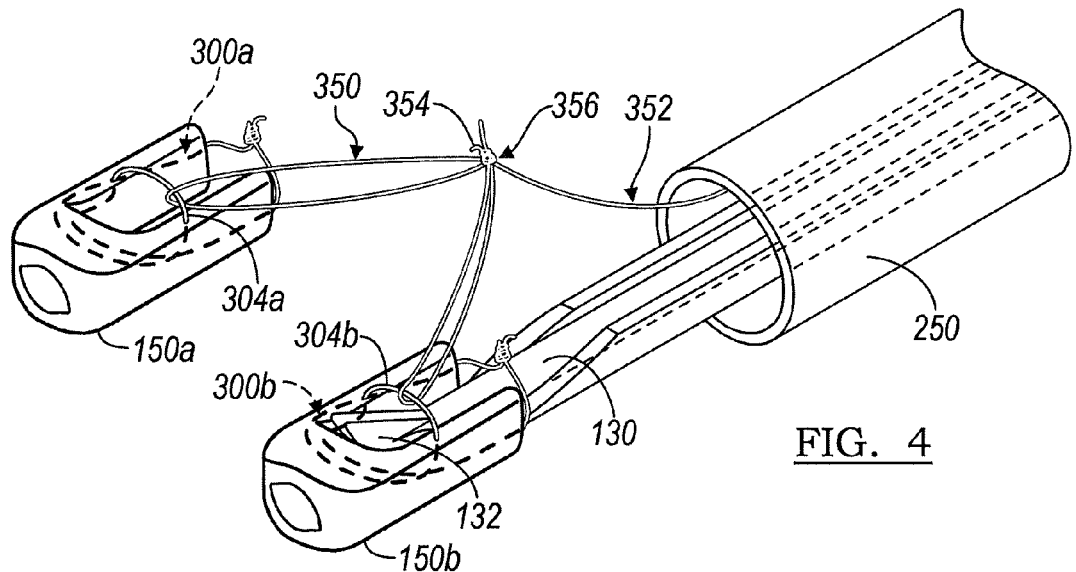
FIG. 4 is a perspective view of the device of FIG. 1, shown in a fourth configuration.

Referring to FIGS. 1-6, the deploying member 130 can include an elastically deformable projection 132, which can be used to push the anchor 150 off the inserter 102. The deploying member 130 can be moved axially along the channel 112 of the inserter 102 by moving a thumb slider 120 of the handle 104 forward or backward relative to the handle 104 of the inserter 102, as shown in FIG. 6. In the assembled position before deployment of either anchor 150a, 150b, the projection 132 of the deploying member 130 can sit behind the first anchor 150a, as shown in FIG. 1. After the first anchor 150a is deployed, the deploying member 130 can be retracted, such that the projection 132 is compressed inward and deformably pulled through the body of second anchor 150b. When the projection 132 exits the second anchor 150b, the projection 132 springs back to its original shape for pushing the second anchor 150b off the inserter 102, as shown in FIGS. 2 and 3. The loops 300a, 300b of the first and second anchors 150a, 150b can be connected with a flexible strand 350 that has a free end 352 and includes a slip knot 356 thereon. The flexible strand 350 can loop around each of the external segments 304a and 304b, as shown in FIG. 4.

An alternative arrangement for coupling the first and second flexible anchors 150a, 150b with a flexible strand forming an adjustable knotless loop is discussed below in reference to FIGS. 20-24.

Figure 9:
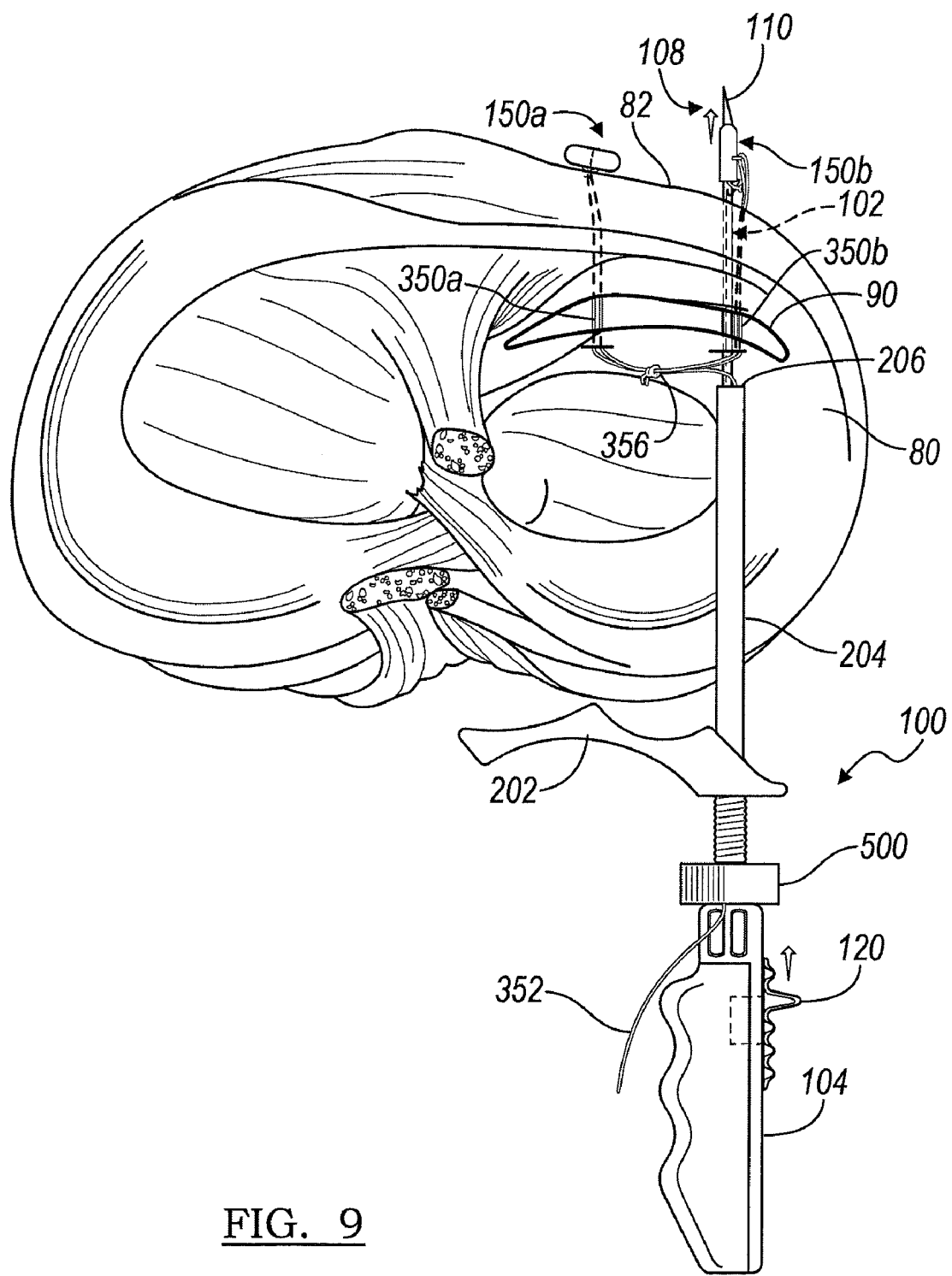
FIG. 9 is an environmental view showing one anchor deployed outside soft tissue according to the present teachings.
Figure 10:
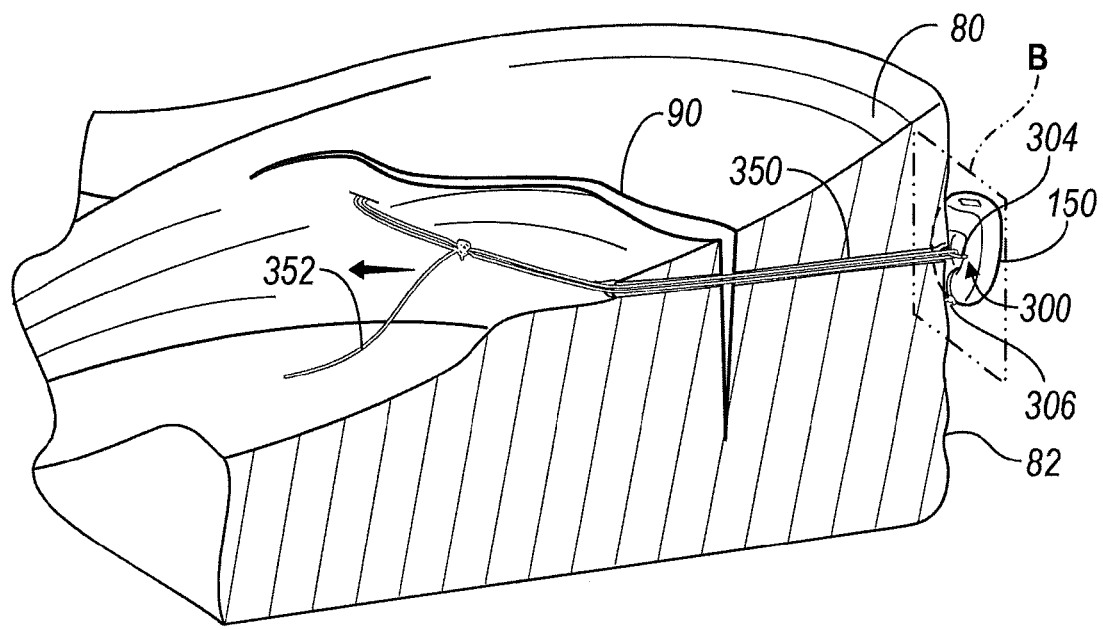
FIGS. 10 and 10A are environmental view showing two anchors deployed outside soft tissue according to the present teachings.

Referring to FIGS. 3-5, 9, and 10, the soft tissue repair device 100 can be used to repair a soft tissue defect 90, such as, for example, a tear, or other weakness in fibrous soft tissue 80, such as in meniscal tissue, cartilage, muscle or other fibrous tissue under the skin. After an outer incision is made through the skin to access the soft tissue 80, the cannula 200 can be positioned through the outer incision without cutting or piercing any tissue and placed adjacent the fibrous soft tissue 80, as shown in FIG. 10. The cannula 200 can, therefore, operate as an access portal for the inserter 102. The inserter 102 can be assembled with the first and second anchors 150a, 150b externally carried thereon, as shown in FIG. 1.

Figure 10A:
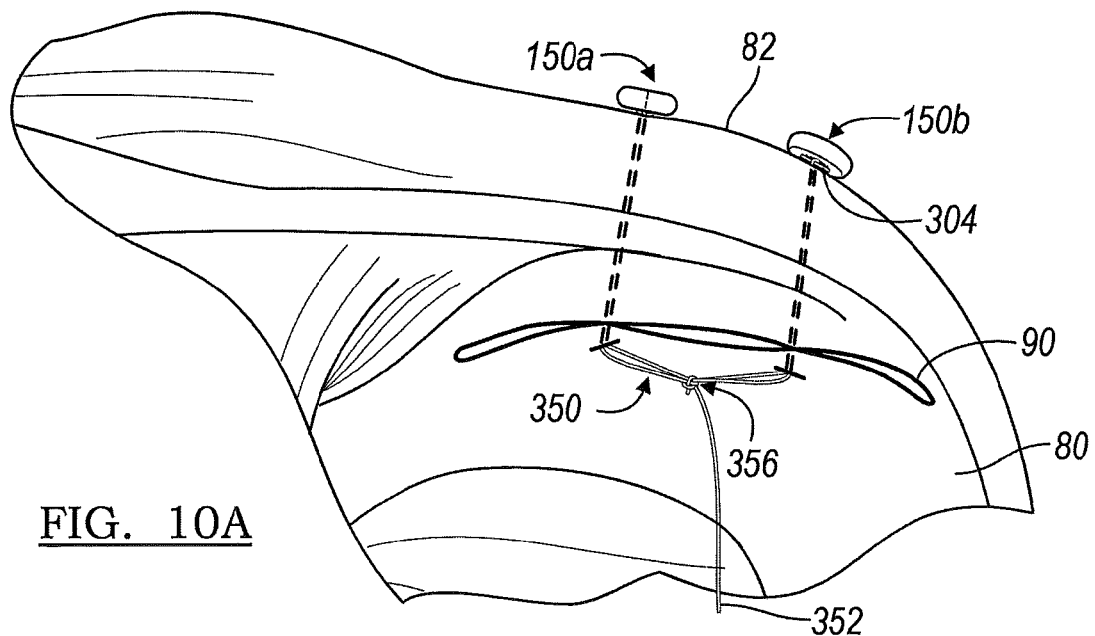
Figure 11:
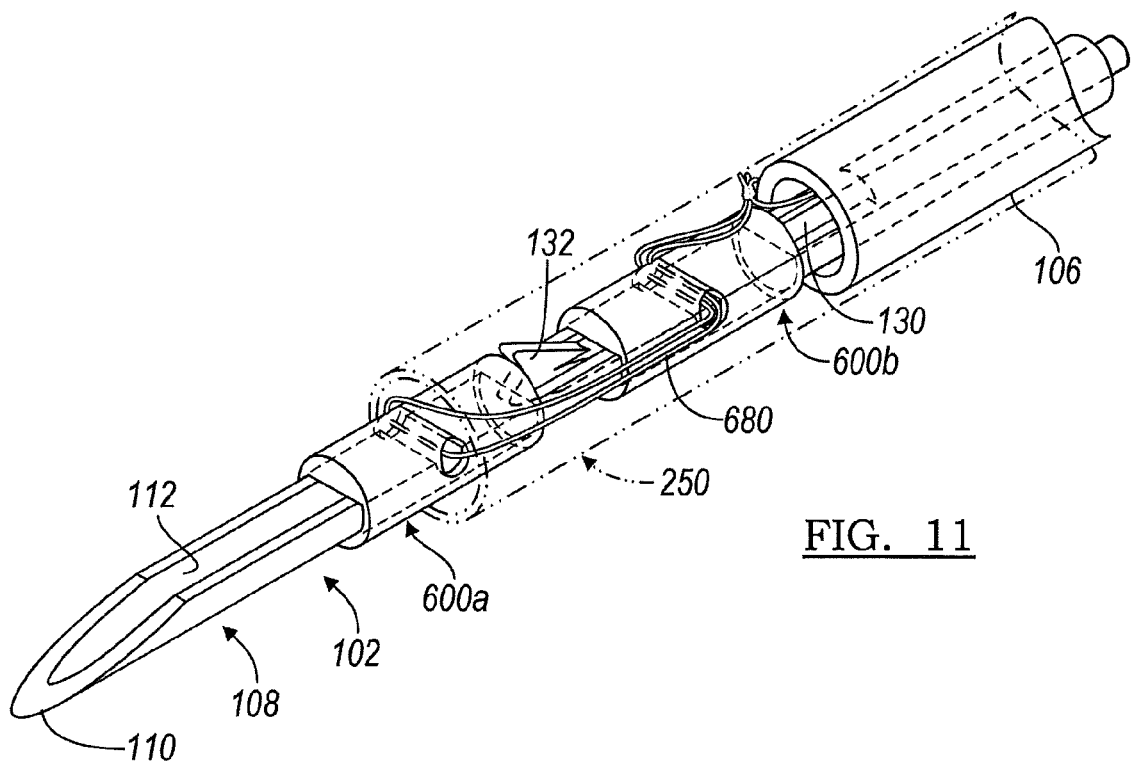
FIG. 11 is a perspective view of a tissue repair device according to the present teachings shown in a first configuration.

Referring to FIGS. 9, 10 and 10A, the inserter 102 can be passed through the cannula 200 and into the soft tissue 80 from a first side of the defect 90 until the distal portion 108 of the inserter 102 can exit a second side 82 of the fibrous soft tissue 80, such as an outer surface or back side of a meniscus of a knee joint or other outer surface of a fibrous tissue, for example. The deploying member 130 can be moved forward relative to the inserter 102, thereby delivering the first anchor 150a on the second side 82 of the soft tissue 80 at a first location, as shown in FIG. 9.

It will be appreciated that the manner and structure of the pre-assembled inserter 102 and anchor 150 allows the anchor 150 to pass through a narrow opening or slit formed in the tissue 80 by the edge 110 of the inserter 102 in a first low-profile folded configuration defining a plane "A", as shown in FIG. 2, and deposited in that configuration outside the tissue 80 with its first and second ends 152, 154 being delivered substantially simultaneously. Further, it will be understood that tightening the first strand loop 300 by pulling on the second external portion 304 can cause the anchor 150 to deform to a second configuration having a substantially flat round-like or knurled shape. Further pulling on the second external portion 304 can rotate the anchor 150 from a first orientation defined by plane A and substantially perpendicular to the outer surface 82 to a second orientation such that the deformed anchor 150 can define a plane "B" substantially parallel to and lying on the outer surface 82 of the soft tissue 80 in a substantially flat shape, as shown in FIG. 10.

Figure 5:
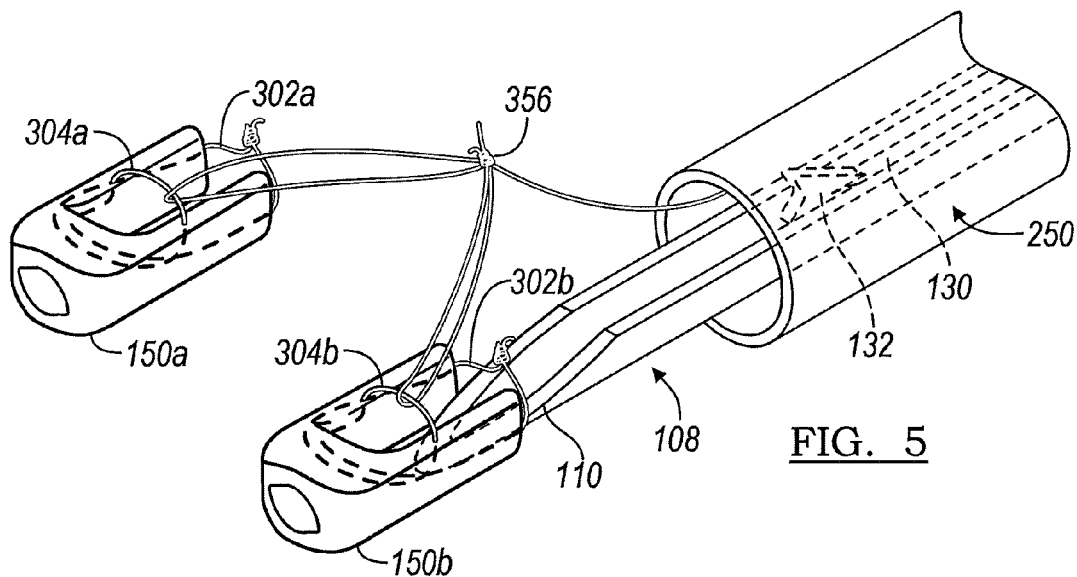
FIG. 5 is a perspective view of the device of FIG. 1, shown in a fifth configuration.

After the first anchor 150a is deployed, the deploying member 130 can be pulled behind the second anchor 150b. The second anchor 150b can be pushed off the distal portion 108 of the inserter 102, as shown in FIGS. 4 and 5, and be delivered to the second side 82 of the soft tissue 80 at a second location, as shown in FIG. 10. The inserter 102 can then be removed. The free end 352 of the strand 350 can be tensioned, thereby deforming the second anchor 150b to a substantially flat round-like or knurled configuration that lays flat on the second side 82 of the soft tissue 80, and compressing the defect 90. Any excess portion of the strand 350 can be cut off.

Figure 12:
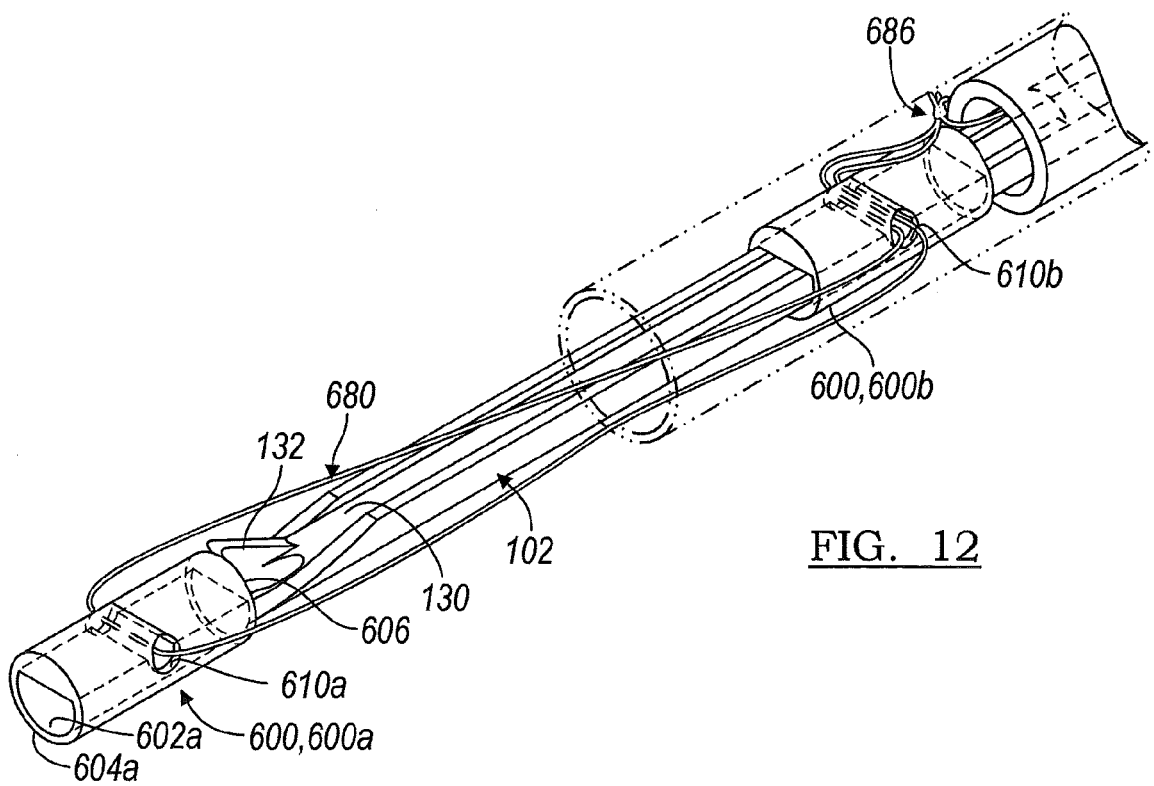
FIG. 12 is a perspective view of the device of FIG. 11, shown in a second configuration.
Figure 13:
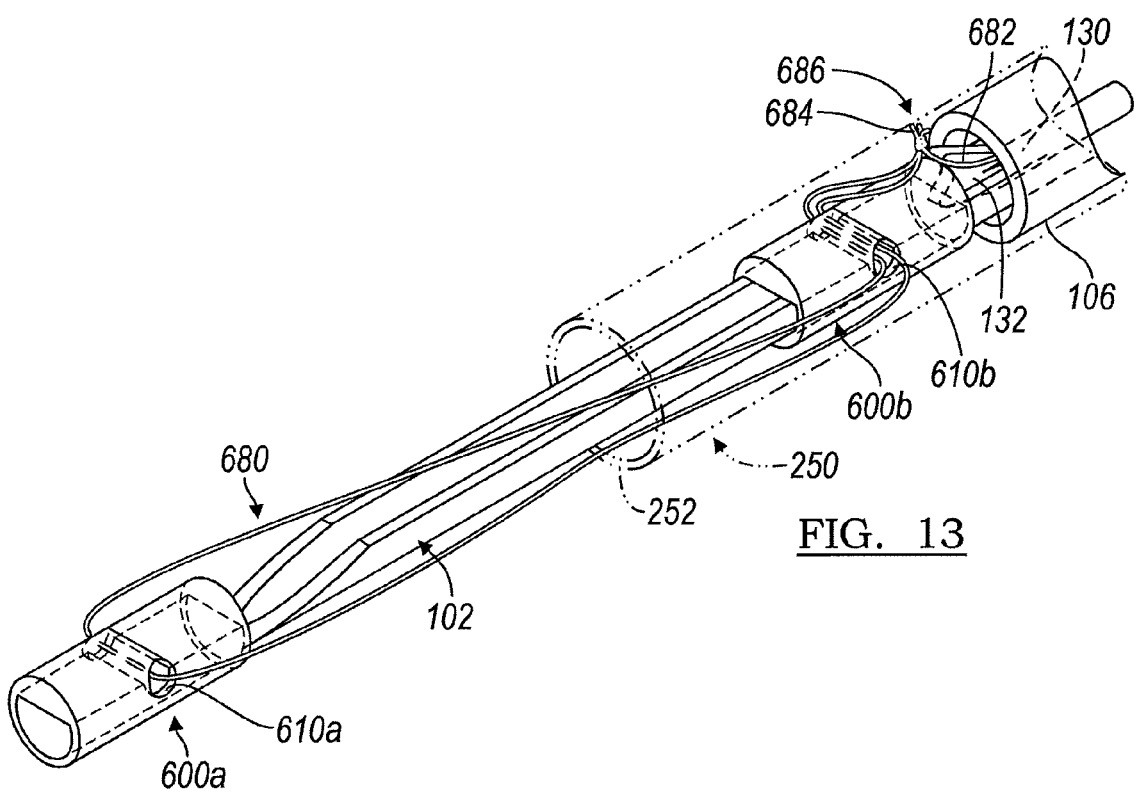
FIG. 13 is a perspective view of the device of FIG. 11, shown in a third configuration.
Figure 13A:
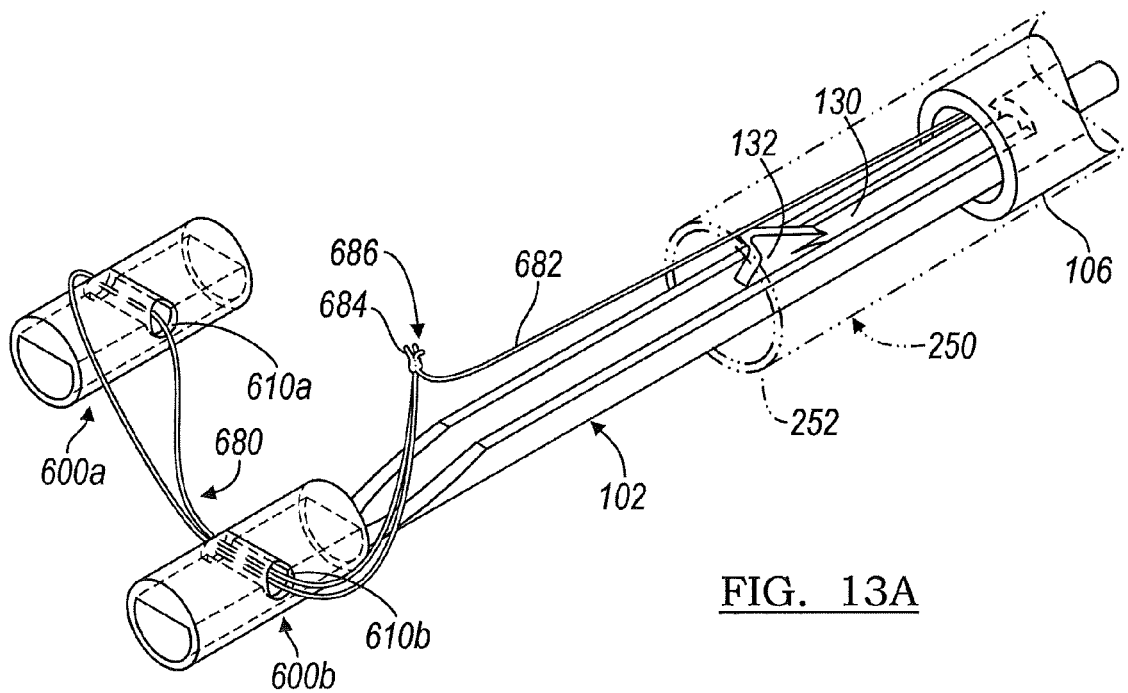
FIG. 13A is a perspective view of the device of FIG. 11, shown in a fourth configuration.

Referring to FIGS. 11-19, a similar procedure can be used to repair a defect 90 in soft tissue 80 using non-deformable or substantially rigid anchors 600, which can be referenced as first and second anchors 600a, 600b, if distinction is desirable for clarity. The anchors 600 can be made of any biocompatible material, such as, for example, titanium or other non-resorbable material, a resorbable or bioabsorbable polymeric or other material, including Lactosorb®, commercially available from Biomet, Inc., Warsaw, Ind. Referring to FIG. 12, each anchor 600 can be a tubular member defining a longitudinal bore 602 (602a, 602b) that extends between first and second ends 604, 606 of the anchor 600. The longitudinal bore 602 can be substantially D-shaped. The ends 604, 606 of the anchor 600 can have rounded edges substantially perpendicular to the anchor 600a, such that the ends 604, 606 are not capable and not intended for piercing or penetrating tissue. The anchor 600 can further define a transverse bore 610 oriented at an angle to the longitudinal bore 602, such as, for example, 90-degrees or other suitable angle relative to the longitudinal bore 602.

The first and second anchors 600a, 600b can be coupled with a flexible strand 680 that passes through the transverse bore 610a of the first anchor 600a. Both ends 682, 684 of strand 680 can be passed through the transverse bore 610b of the second anchor 600b and tied to a slip knot 686, leaving one free end 682 for tightening the strand 680, as shown in FIGS. 11-13A.

Figure 14:
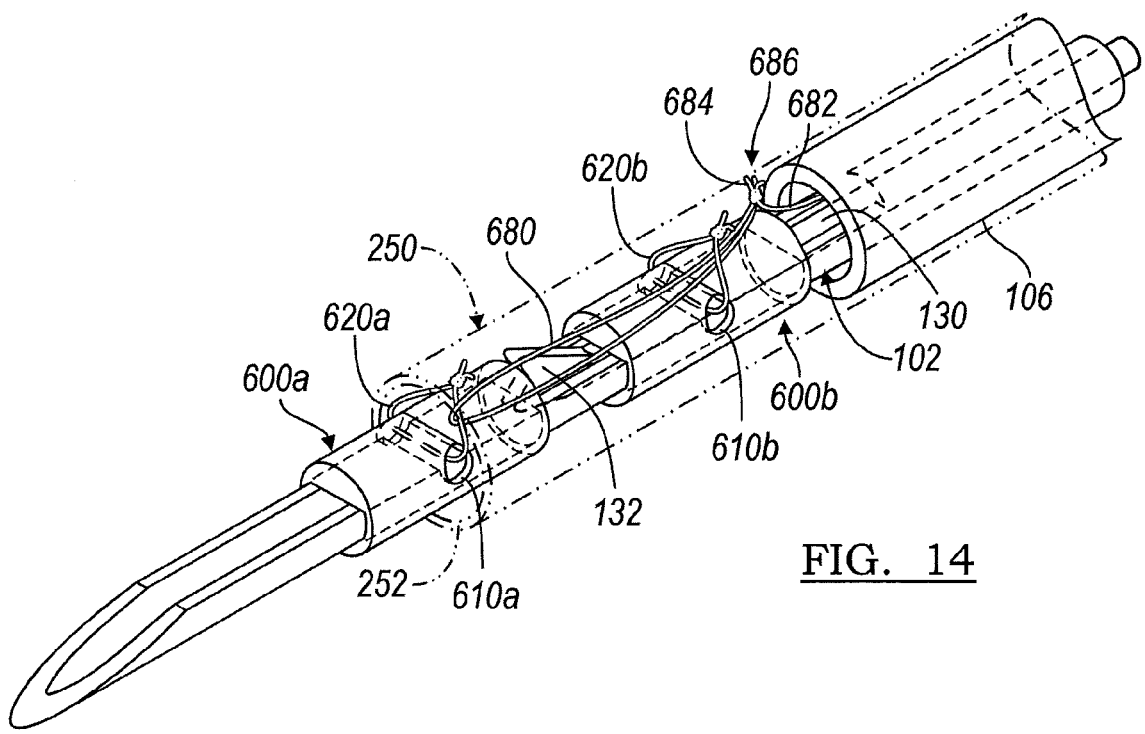
FIG. 14 is a perspective view of a tissue repair device, according to the present teachings, shown in a first configuration.
Figure 14A:
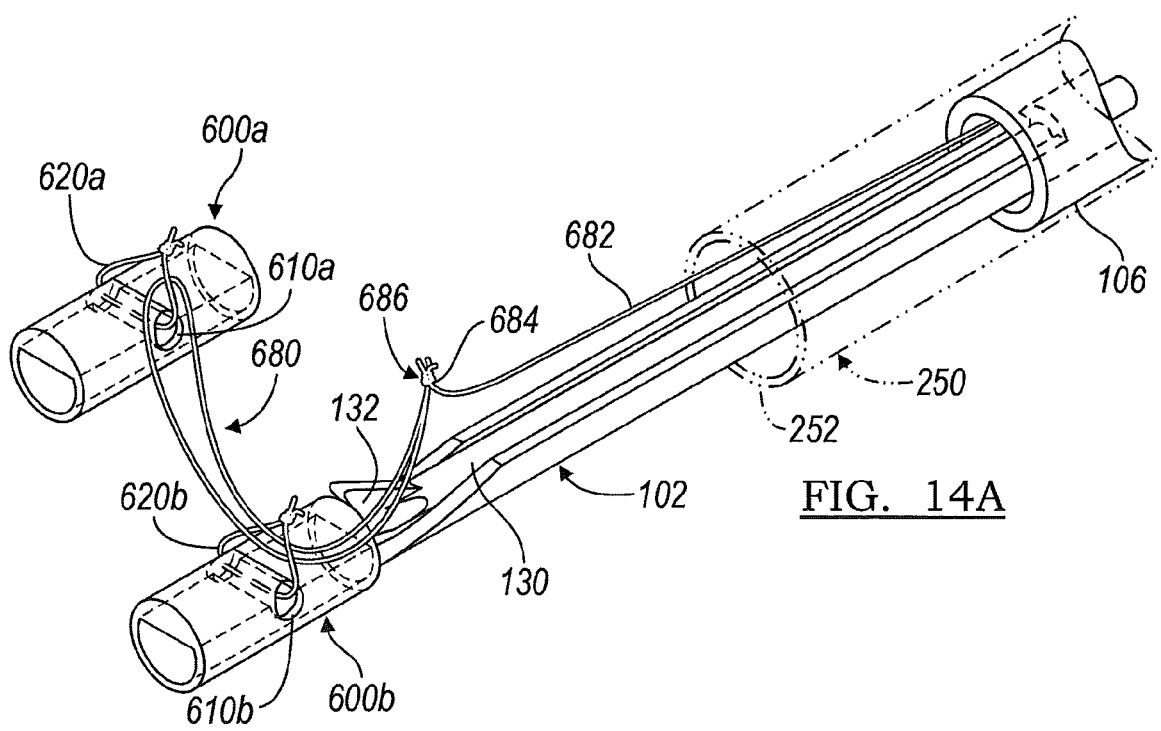
FIG. 14A is a perspective view of the device of FIG. 14, shown in a second configuration.
Figure 15:
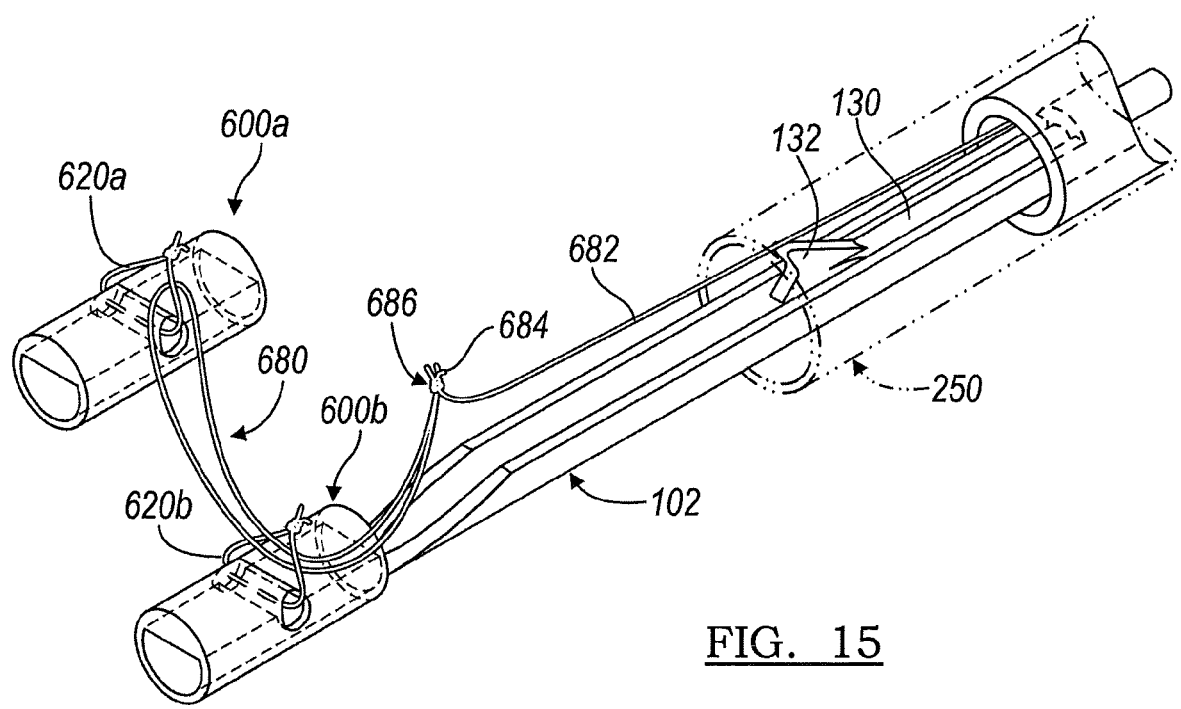
FIG. 15 is a perspective view of the device of FIG. 14, shown in a third configuration.

Alternatively, flexible strand loops 620a and 620b can be formed through the respective transverse bores 610a, 610b of the first and second anchors 600a, 600b, as shown in FIG. 14. A flexible strand 680 can then be used to connect the two loops 620a, 620b, as shown in FIGS. 14A and 15.

Figure 18:
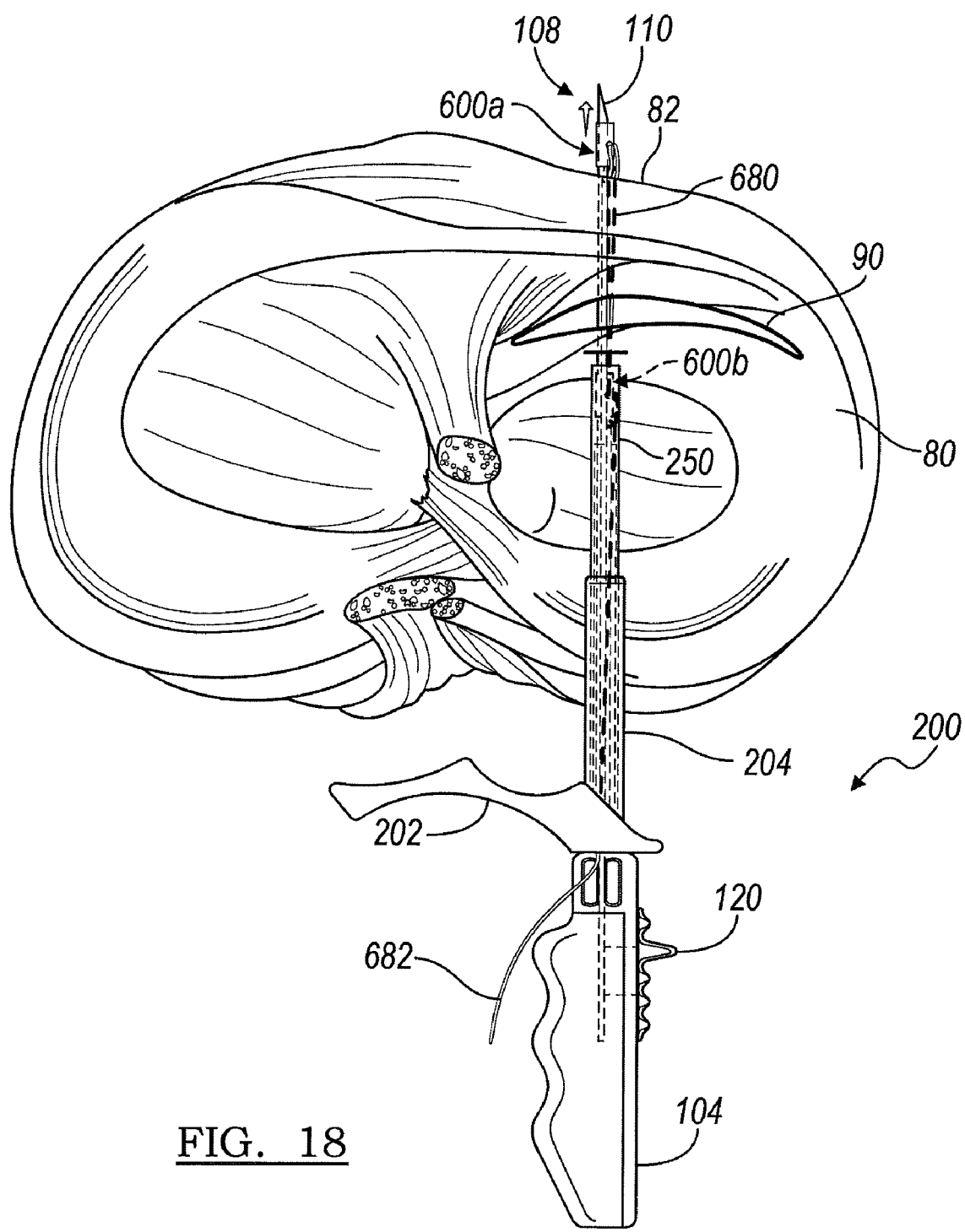
FIG. 18 is an environmental view showing one anchor deployed outside soft tissue according to the present teachings.

Referring to FIGS. 16-19A, the anchor 600 can be inserted through fibrous tissue using the inserter 102 with the cannula 200, and can be used for fibrous soft tissue repair as described above. In one exemplary procedure, the inserter 102 can be passed through the cannula 200 into the soft tissue 80 from a first side of the defect 90 until the distal portion 108 of the inserter 102 can exit a second side 82 of the soft tissue 80, such as an outer surface or back side of a meniscus of a knee joint or other outer surface of a fibrous tissue, for example. The deploying member 130 can be moved forward thereby delivering the first anchor 600a on the second side 82 of the soft tissue 80 at a first location, as shown in FIG. 18.

Figure 19:
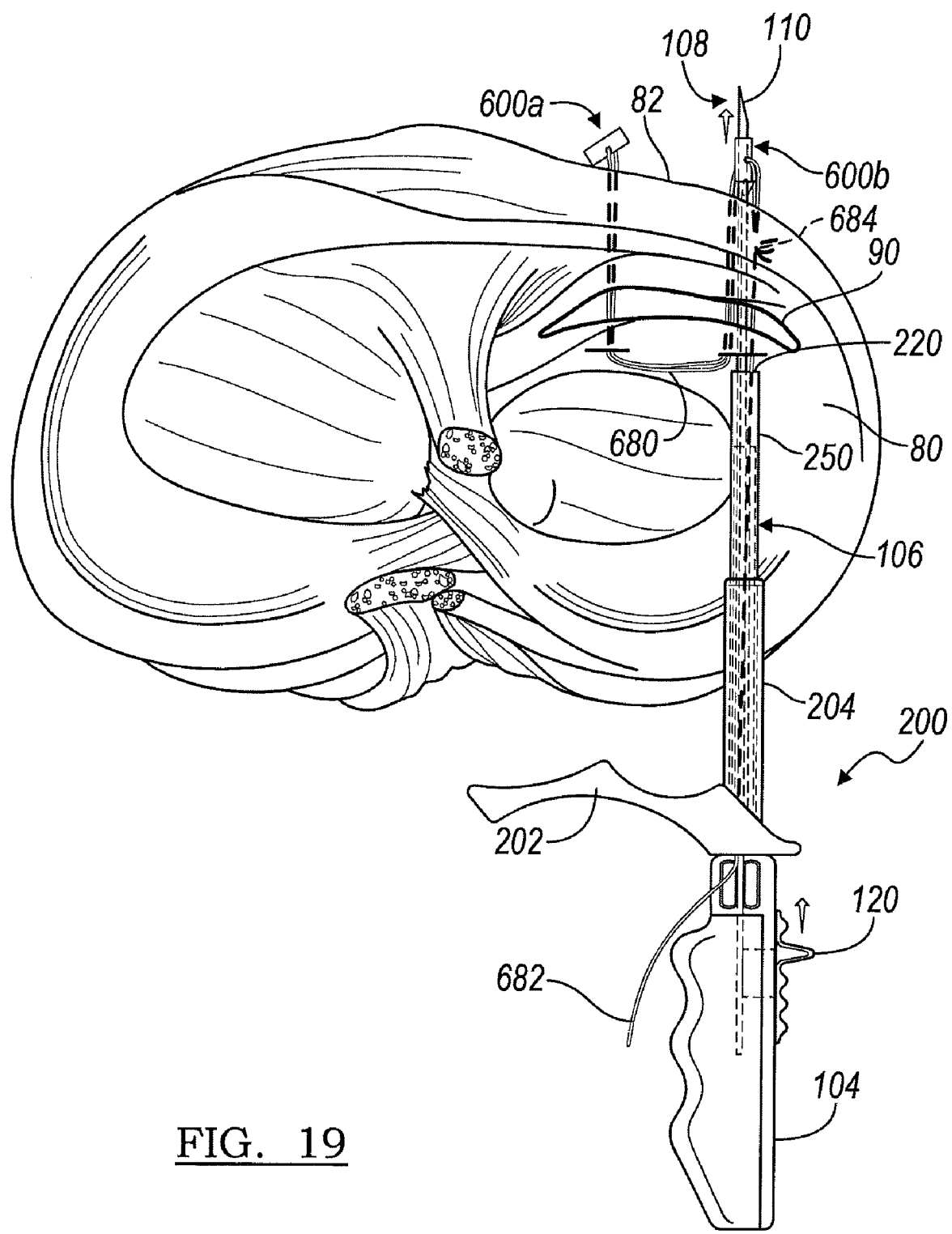
FIGS. 19 and 19A are environmental views showing two anchors deployed outside soft tissue according to the present teachings.
Figure 19A:
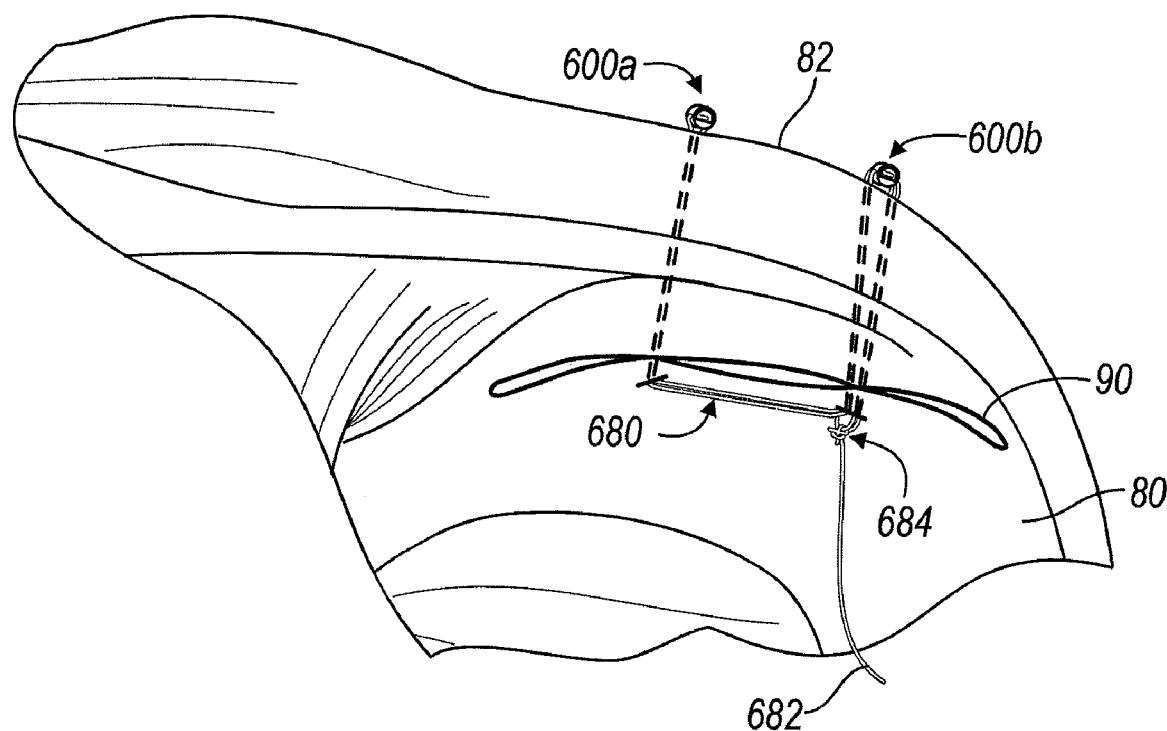
Figure 20:
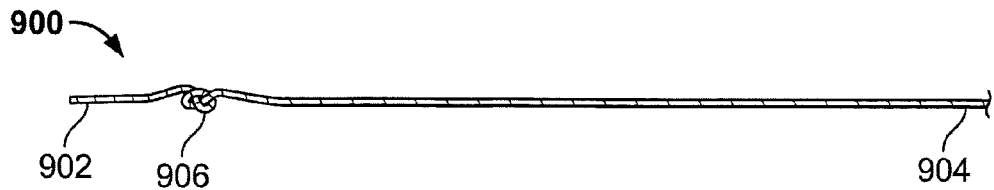
FIGS. 20, 21, 22, and 23 are sequential views illustrating an exemplary method of coupling first and second flexible anchors with a flexible strand.

The deploying member 130 can then be pulled behind the second anchor 600b, as the projection 132 is compressed inward and passes through the bore 602b of the second anchor 600b. After the projection 132 exits the second anchor 600b, the projection springs back to is original shape behind the second anchor 600b. The second anchor 600b can be pushed off the distal portion 108 of the inserter and be delivered to the second side 82 of the soft tissue 80 at a second location, as shown in FIG. 19. The inserter 102 can then be removed. The free end 682 of the strand 680 can be tensioned, thereby rotating the anchors 600a, 600b, such that each anchor 600a, 600b is positioned with its longitudinal axis parallel to the surface of the second side 82 of the soft tissue 80, as shown in FIG. 19A. Tensioning the strand 680 further can compress the defect 90. Any excess portion of the strand 380 can be cut off.

Alternative non-deformable anchors and loop arrangements are discussed below in reference with FIGS. 25A-27.

Figure 21:
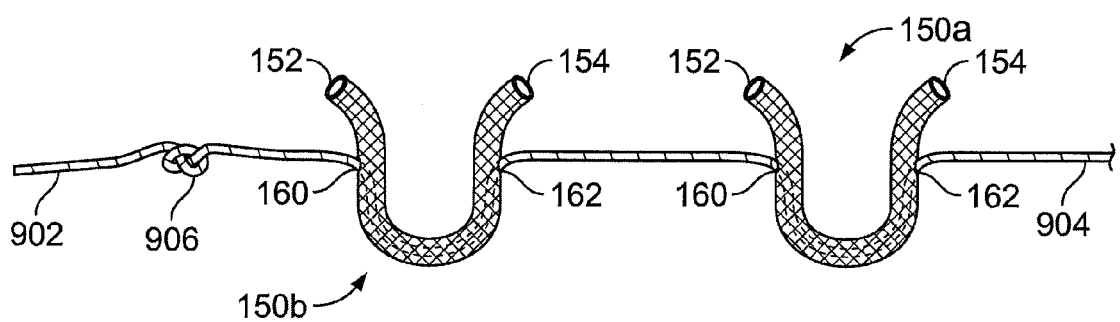

Referring to FIGS. 20-24, another aspect of coupling the flexible anchors 150a, 150b with a flexible strand 900 is illustrated. The flexible strand 900 can have first and second ends 902, 904 and can be made of materials similar to those discussed above in reference to the flexible strand 301. The flexible strand 900 can be braided in a tubular or hollow form such that it forms an internal passage 901 between the first and second ends 902, 904. A small knot or other retaining device 906 can be optionally formed adjacent the first end 902. The flexible strand 900 can be passed through a first opening 160 of each of the flexible anchors 150a, 150b, guided along the corresponding bore 158 and exit through a second opening 162 of each flexible anchor 150a, 150b, as shown in FIG. 21. The openings 160, 162 can be positioned intermediately between the first and second ends 152, 154 of each flexible anchor 150a, 150b at a distance of, for example, one-quarter length from the ends 152, 154 of each flexible anchor 150a, 150b. Furthermore, it will be appreciated that the openings 160, 162 can be apertures or voids in the woven fabric of the flexible anchors 150a, 150b, such that the openings 160, 162 do disrupt or break the weave of flexible anchors 150a, 150b, when the flexible anchor 150a, 150b are made of braided or woven material.

Figure 22:
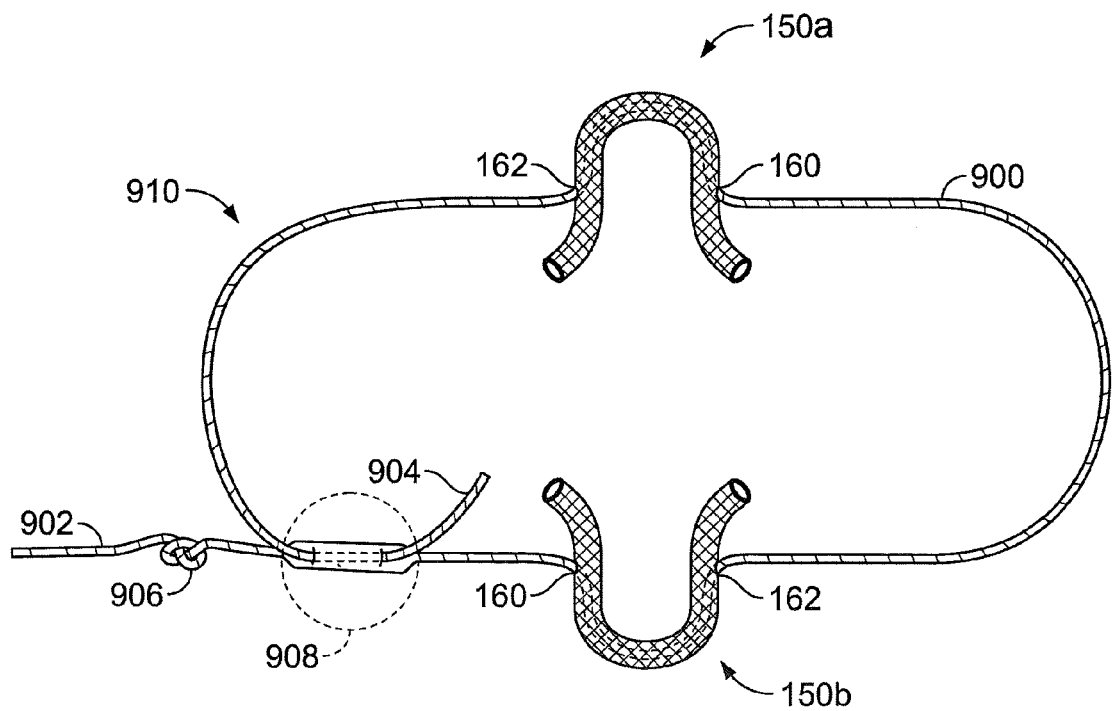
Figure 22A:
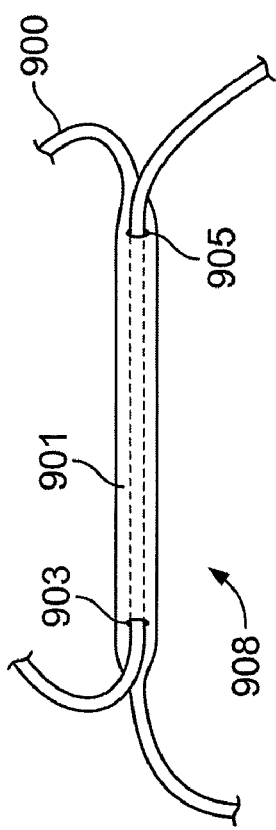
FIG. 22A shows a detail of FIG. 22.
Figure 23:
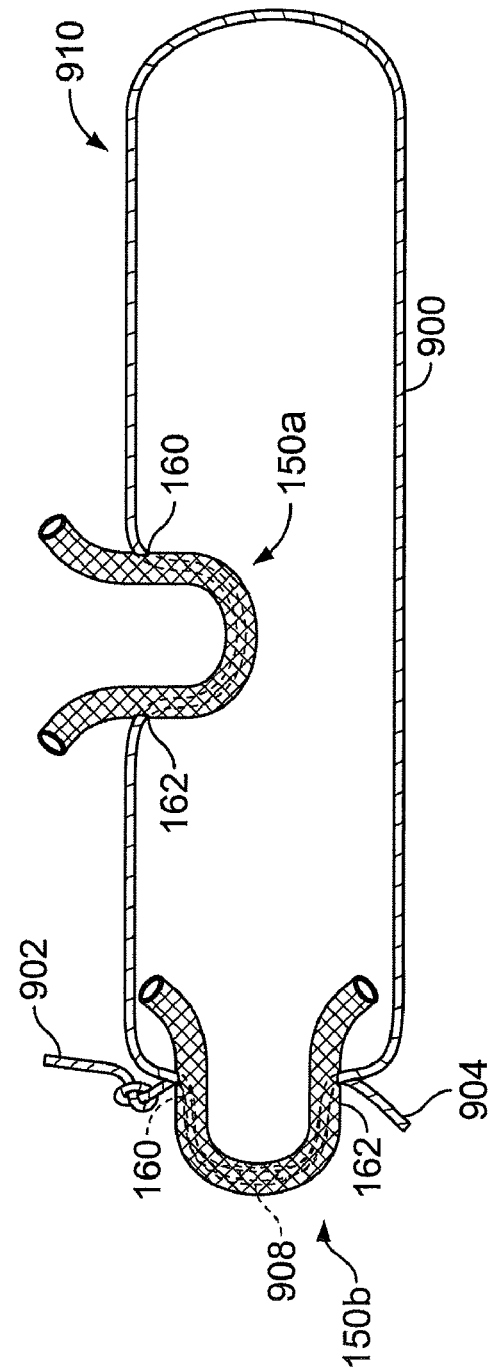
Figure 25A:
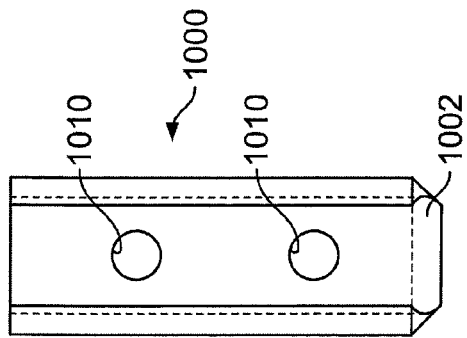
FIG. 25A is a bottom view of an anchor according to the present teachings.
Figure 25B:
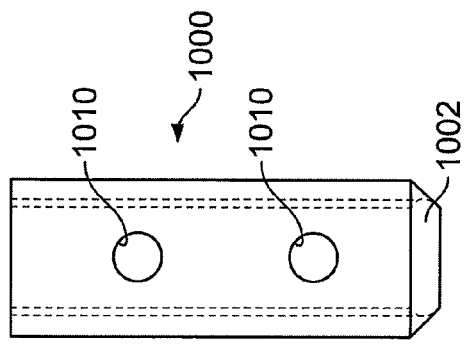
FIG. 25B is a top view of the anchor of FIG. 25A.
Figure 24:
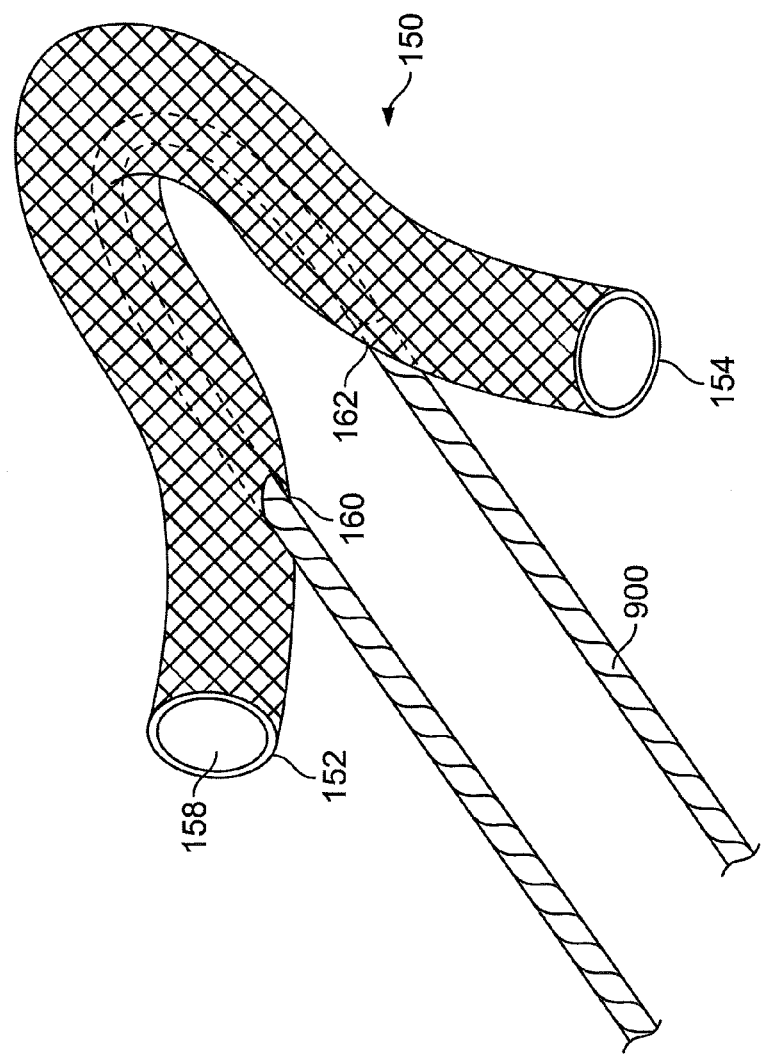
FIG. 24 is a perspective view of a flexible anchor coupled with a flexible strand.

After the flexible anchors 150a, 150b are mounted on the flexible strand 900, the second end 904 of the flexible strand 900 can be inserted into the internal passage 901 of the flexible strand 900 at an aperture 903, guided longitudinally along the passage 901, and led out of the passage 901 of the flexible strand 900 at an aperture 905. The portion of the strand 900 between apertures 901 and 905 can form an adjustment portion 908 between the optional knot 906 and the opening 160 of the second flexible anchor 150b, such that the flexible strand 900 defines a single adjustable knotless loop 910, as shown in FIGS. 22 and 22A. The second flexible anchor 150b can be slidably moved along the flexible strand 900 until the adjustment portion 908 is within the bore 158 of the second flexible anchor 150b and the knot 906 is adjacent the opening 160 of the second flexible anchor 150b, as shown in FIG. 23. It will be appreciated, however, that the adjustment portion 908 can remain in the position shown in FIG. 22.

The adjustable knotless loop 910 is self-locking and does not require the surgeon to tie a knot during the surgical procedure for securing the flexible strand 900. Further, once the adjustable knotless loop 910 is self-locked by pulling the second end 904 of the flexible strand 900 and tensioning the flexible strand 900, friction prevents the adjustable knotless loop 910 from being loosened, thereby providing a secure lock. Additional details regarding forming the knotless adjustable loop 910, and additional adjustable knotless loop configurations are disclosed in co-pending and commonly assigned U.S. patent application Ser. No. 11/541,506, filed on Sep. 29, 2006, the disclosure of which is incorporated herein by reference.

The first and second flexible anchors 150a, 150b can be loaded on the inserter 102, as shown in FIG. 1 and discussed above, coupled with the flexible strand 900, which forms the closed adjustable knotless loop 910. Pulling the second end 904 of the flexible strand 900 can deform the first and second flexible anchors 150a, 150b for anchoring, and shorten the length of the adjustable knotless loop 910 without using a slipknot. The inserter 102 with the flexible anchors 150a, 150b pre-loaded thereon can be used for repairing soft tissue 80, such as a meniscus tear 90, in a similar manner as discussed with reference to FIG. 9, for example. The thumb slider 120 can be moved forward to deploy the first flexible anchor 150a at an outer surface 82 of the soft tissue. The thumb slider 120 can then be moved backward, enabling the deploying member 130 to be retracted to a position for deploying the second flexible anchor 150b at the outer surface 82 of the soft tissue and adjacent the first flexible anchor 150a. Pulling the second end 904 of the flexible strand 900 can tighten the adjustable knotless loop 910, secure the first and second flexible anchors 150a, 150b against the outer surface 82 of the soft tissue 80 and reduce the defect 90. Further, the portions of the sleeve between the first and second ends 152, 154 of each of the flexible anchors 150a, 150b and the corresponding first and second openings 160, 162, define anchoring leg portions that provide additional resistance for securing the flexible anchors 150a, 150b on the outer surface 82 of the soft tissue 80, as these leg portions are forced against the outer surface 82 for anchoring.

Figure 26:
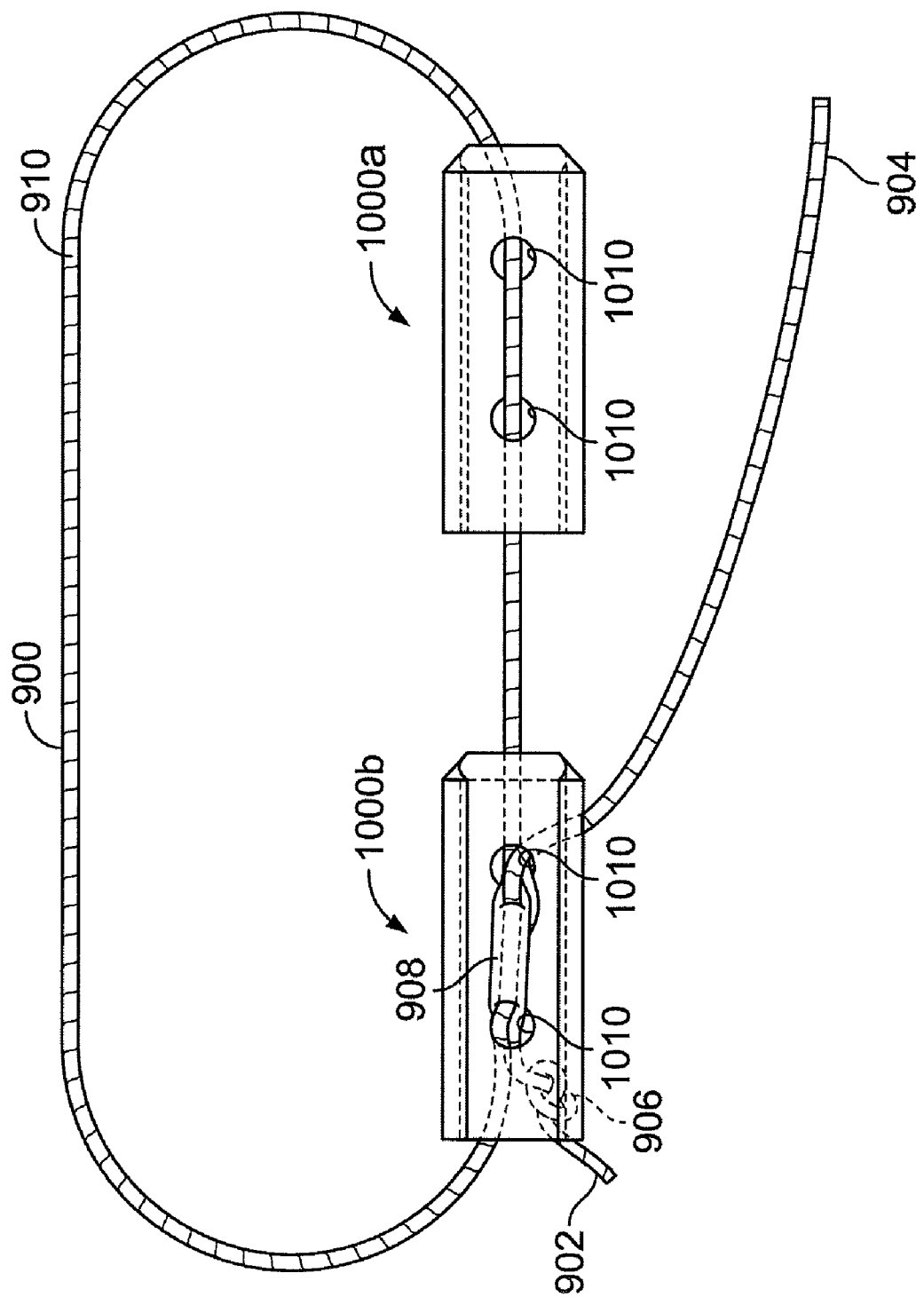
FIG. 26 is a view illustrating coupling first and second anchors with a flexible strand according to the present teachings.

Referring to FIGS. 25A-27, another non-deformable or substantially rigid anchor 1000 is illustrated. Similarly to the anchors 600a, 600b illustrated in FIG. 11, the anchor 1000 can be made of any biocompatible material, such as, for example, titanium or other non-resorbable or resorbable material, including polymeric materials and Lactosorb® commercially available from Biomet, Inc., Warsaw, Ind., and can be similarly used to repair a soft tissue defect 90. The anchor 1000 can be tubular defining a longitudinal bore 1002 that extends between first and second ends 1004, 1006 of the anchor 1000, and can have an open, channel-like cross-section defining an arc of 180 degrees or more. The ends 1004, 1006 of the anchor 1000 can have blunt rounded edges substantially perpendicular to the anchor 1000, such that the ends 1004, 1006 are not capable and not intended for piercing or penetrating tissue. The anchor 1000 can further define first and second through bores 1010 oriented substantially perpendicularly to the anchor 1000 and communicating with the longitudinal bore 1002. A flexible strand 900 can be passed through the through bores 1010 coupling the first and second anchors 1000a, 1000b with an adjustable knotless loop 910, as shown in FIG. 26. The strand 900 can be tightened by pulling on the second end 904 of the flexible strand 900 without using a slipknot, as discussed above.

Figure 27:
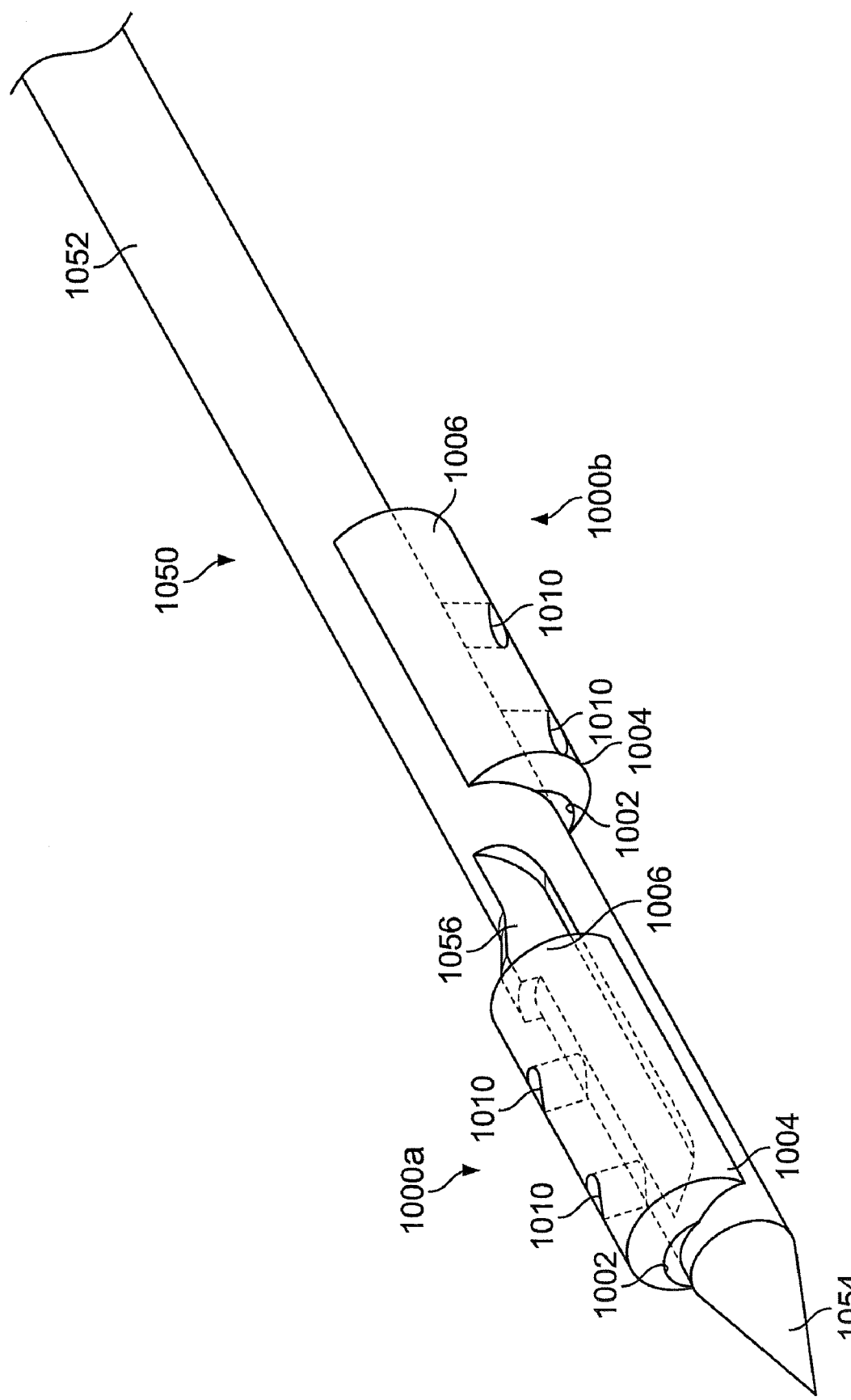
FIG. 27 is a perspective view showing first and second anchors loaded onto an inserter according to the present teachings.

The first and second anchors 1000a, 1000b, coupled with the flexible strand 900, can be mounted on a single inserter 102, as described above in connection with FIG. 11. Another exemplary inserter 1050 for use with the first and second anchors 1000a, 1000b is shown in FIG. 27. The inserter 1050 can have a cylindrical body 1052, a pointed distal tip 1054, and a stop 1056. The first anchor 1000a can be mounted externally onto the body 1052 of the inserter 1050 between the tip 1054 and the stop 1056, such that a portion of the inserter 1052 is received in the longitudinal bore 1002 of the first anchor 1000a. The second anchor 1000b can be similarly mounted externally onto the body 1052 of the inserter 1050 behind the first anchor 1000a and facing in a direction opposite to the first anchor 1000a and opposite to the stop 1056.

In use, the inserter 1050 can be pushed through the soft tissue 80 and through the defect 90 to the outer surface 82 of the soft tissue 80 carrying the first anchor 1000a therethrough. The stop 1056 prevents the anchor 1000a from sliding backward when the inserter 1050 is retracted out of the soft tissue 80, leaving the first anchor 1000a on the outer surface 82. The second anchor 1000b can be then slid along the body 1052 of the inserter 1050 opposite the stop 1056, rotated about 180 degrees to be positioned directly behind the stop 1056 and deployed off the inserter 1050 similarly to the deployment of the first anchor 1000a. In one aspect, the anchors 1000a and 1000b can be mounted in a keyed manner onto the inserter 1050, such that accidental relative rotation can be substantially prevented without preventing intentional sliding and rotation of the anchors. In a related aspect, more than two anchors can be loaded on the inserter 1050. Two additional anchors, for example, can be loaded behind the stop 1056. In this aspect, the four anchors can be loaded at 90-degrees circumferentially apart on the inserter 1050, and can be deployed sequentially, with a 90-degree relative rotation of the inserter 1050 relative to each anchor, after deployment of the previous anchor.

It will be appreciated from the above description and drawings that the present teachings provide anchors of versatile configurations that can be passed through tissue easily in a compact or low profile configuration and or orientation and then positioned outside tissue in a second orientation that provides anchoring without tissue penetration, preventing withdrawal from the tissue and reducing tissue injury. Further, the use of an inserter provided with preassembled anchors can help reduce the time length of the procedure and simplify manipulations required during the procedure.

It will be further understood that the various embodiments of the inserters, anchors and coupling arrangements can be mixed and matched or combined in ways other than those explicitly discussed above, without departing from the scope of the present teachings.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method for repairing a defect in a fibrous soft tissue comprising:
   passing a distal portion of an inserter through a longitudinal bore of a first anchor;
   passing the distal portion of the inserter through a longitudinal bore of a second anchor;
   positioning a deploying member having a movable projection within a longitudinal channel of the inserter having an open cross-section along a longitudinal axis of the inserter such that the projection is between the first anchor and the second anchor, the projection movable between a first position protruding transverse to the longitudinal channel against the first anchor for expelling the first anchor and a second position for passing the projection through the longitudinal bore of the second anchor;
   coupling first and second anchors with a flexible strand; and
   tensioning the flexible strand to reduce the defect.

2. A method for repairing a defect in a fibrous soft tissue comprising:
   passing a distal portion of an inserter having a longitudinal channel through a longitudinal bore of a first anchor;
   passing the distal portion of the inserter through a longitudinal bore of a second anchor;
   positioning a deploying member having a deformable projection within the longitudinal channel;
   coupling first and second anchors with a flexible strand; and
   tensioning the flexible strand to reduce the defect.

3. The method of claim 2, wherein the longitudinal bore of each of the first and second anchors is keyed to the distal portion of the inserter.

4. The method of claim 3, wherein the longitudinal bore of each of the first and second anchors is D-shaped.

5. The method of claim 2, wherein positioning the deploying member includes sliding the deploying member within the longitudinal channel.

6. The method of claim 5, further comprising positioning the deformable projection between the first and second anchors.

7. The method of claim 6, wherein the projection is configured to be capable of pushing the first anchor out of the inserter.

8. The method of claim 7, wherein the projection is configured to be retractable through the longitudinal bore of the second anchor.

9. The method of claim 8, wherein the projection is configured to be capable of pushing the second anchor out of the inserter.

10. The method of claim 6, wherein the projection is configured to be capable of deploying the first and second anchors sequentially.

11. The method of claim 2, further comprising passing the flexible strand through an opening of the first anchor and through an opening of the second anchor.

12. The method of claim 11, wherein the opening of the first anchor is a transverse bore perpendicular to a longitudinal axis of the first anchor.

13. The method of claim 2, further comprising passing the flexible strand through first and second strand loops respectively coupled to the first and second anchors.

14. The method of claim 13, wherein the first strand loop passes through a transverse bore defined in the first anchor and the second strand loop passes through a transverse bore defined in the second anchor.

15. A method for repairing a defect in a fibrous soft tissue, the method comprising:
   inserting a distal portion of an inserter through a defect of the fibrous soft tissue to an outer surface of the fibrous soft tissue;
   moving a deploying member along a longitudinal channel of the inserter, wherein the longitudinal channel has an open cross-Section along a longitudinal axis of the inserter;
   pushing a first tubular anchor out of the distal portion of the inserter with a projection of the deploying member;

retracting the deploying member by moving the projection from a first position protruding transverse to the longitudinal channel of the inserter in front of a second tubular anchor to a second position for passing the projection through a longitudinal bore of the second tubular anchor;

placing the projection of the deploying member against and behind the second tubular anchor;

pushing the second tubular anchor out of the distal portion of the inserter with the projection of the deploying member; and tensioning a flexible strand coupling the first and second anchors such to reduce the defect.

16. A method for repairing a defect in a fibrous soft tissue, the method comprising:

inserting a distal portion of an inserter through a defect of the fibrous soft tissue to an outer surface of the fibrous soft tissue;

moving a deploying member along a longitudinal channel of the inserter;

pushing a first tubular anchor out of the distal portion of the inserter with a projection of the deploying member;

expelling the first tubular anchor from the distal portion of the inserter at a first location on an outer surface of the fibrous soft tissue, wherein the distal portion of the inserter passes through a longitudinal bore of the first tubular anchor;

elastically deforming the projection by passing the projection through a longitudinal bore of a second anchor in the longitudinal channel of the inserter;

expelling the second tubular anchor from the distal portion of the inserter at a second location on the outer surface of the fibrous soft tissue; and tensioning a flexible strand coupling the first and second anchors to reduce the defect.

17. The method of claim 16, wherein the longitudinal bore is D-shaped.

18. The method of claim 16, further comprising:

retracting the inserter from the defect at a third location after expelling the first anchor; and inserting the inserter through the defect at a fourth location before expelling the second anchor.

19. A method for repairing a defect in a fibrous soft tissue, the method comprising:

positioning a cannula through an incision adjacent to fibrous soft tissue;

passing an inserter through the cannula;

inserting a distal portion of the inserter through a defect of the fibrous soft tissue to an outer surface of the fibrous soft tissue;

moving a deploying member relative to a channel of the inserter against a first anchor, the first anchor having a longitudinal passage through which the distal portion of the inserter is received;

expelling the first anchor from the inserter on the outer surface of the fibrous soft tissue using the deploying member;

retracting the deploying member through a longitudinal passage of a second anchor, the second anchor mounted on the distal portion of the inserter;

elastically deforming a projection of the deploying member while retracting the deploying member through the longitudinal passage of the second anchor;

moving the deploying member relative to the channel of the inserter against the second anchor;

expelling the second anchor from the inserter on the outer surface of the fibrous soft tissue using the deploying member;

tensioning a flexible strand coupling the first and second anchors; and reducing the defect.

20. The method of claim 19, wherein the first and second anchors are substantially rigid anchors.

21. The method of claim 19, wherein inserting the inserter through the defect includes inserting the inserter through the defect at a first location and expelling the first anchor at a second location and inserting the inserter through the defect at a third location and expelling the second anchor at a fourth location.

* * * * *

UNITED STATES PATENT AND TRADEMARK OFFICE
CERTIFICATE OF CORRECTION

PATENT NO. : 8,292,921 B2
APPLICATION NO. : 13/045691
DATED : October 23, 2012
INVENTOR(S) : Kevin T. Stone et al.

It is certified that error appears in the above-identified patent and that said Letters Patent is hereby corrected as shown below:

In the Specification

Column 1, lines 10-11, "January 6, 2007" should be --January 16, 2007--.

Column 1, line 21, "April 20, 2006." should be --April 20, 2006,--.

Column 2, line 51, "view" should be --views--.

In the Claims

Column 10, line 64, Claim 15, "cross-Section" should be --cross-section--.

Signed and Sealed this
Twenty-ninth Day of October, 2013

Teresa Stanek Rea
*Deputy Director of the United States Patent and Trademark Office*